(12) United States Patent
Ni et al.

(10) Patent No.: US 11,984,292 B2
(45) Date of Patent: May 14, 2024

(54) RADIOTHERAPY DEVICE AND MICROWAVE SOURCE THEREOF

(71) Applicant: SHANGHAI UNITED IMAGING HEALTHCARE CO., LTD., Shanghai (CN)

(72) Inventors: Cheng Ni, Shanghai (CN); Gang Pan, Shanghai (CN); Zhangfan Deng, Shanghai (CN); Mingyuan Song, Shanghai (CN); Zongrui Sun, Shanghai (CN); Haoshan Zhu, Shanghai (CN); Feichao Fu, Shanghai (CN); Jincheng Mei, Shanghai (CN); Chengjia Yuan, Shanghai (CN); Li Wang, Shanghai (CN); Xiaofeng Zhang, Shanghai (CN); Jianxiong Zou, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/146,438

(22) Filed: Dec. 26, 2022

(65) Prior Publication Data
US 2023/0154716 A1    May 18, 2023

Related U.S. Application Data

(63) Continuation of application No. PCT/CN2021/087063, filed on Apr. 13, 2021.

(30) Foreign Application Priority Data

Jul. 27, 2020  (CN) .......................... 202010731106.4
Feb. 10, 2021  (CN) .......................... 202110184055.2
Mar. 10, 2021  (CN) .......................... 202120513013.4

(51) Int. Cl.
*H01J 1/22*    (2006.01)
*H01J 35/06*   (2006.01)

(52) U.S. Cl.
CPC .............. *H01J 1/22* (2013.01); *H01J 35/064* (2019.05)

(58) Field of Classification Search
CPC .................................. H01J 1/22; H01J 35/064
See application file for complete search history.

(56) References Cited

U.S. PATENT DOCUMENTS 2,141,933 A   12/1938  Perrott
5,130,601 A    7/1992  Walker et al.
(Continued)

FOREIGN PATENT DOCUMENTS

CN        1034823 A     8/1989
CN        1889224 A     1/2007
(Continued)

OTHER PUBLICATIONS

International Search Report in PCT/CN2021/087063 dated Jul. 1, 2021, 4 pages.
(Continued)

*Primary Examiner* — Mary Ellen Bowman
(74) *Attorney, Agent, or Firm* — METIS IP LLC

(57) ABSTRACT

The present disclosure is related to a microwave source. The microwave source may include a cathode heater and a thermionic emitter. The cathode heater may include a first component, and a second component enclosing at least a portion of the first component. The thermionic emitter may be configured to release electrons when the thermionic emitter is heated by the cathode heater. At least a portion of the second component of the cathode heater may be in contact with the thermionic emitter.

20 Claims, 20 Drawing Sheets

(56) References Cited

U.S. PATENT DOCUMENTS

| | | | |
|---|---|---|---|
| 5,350,969 A * | 9/1994 | Gattuso | H01J 1/22 313/340 |
| 2003/0164667 A1 | 9/2003 | Ricaud | |
| 2007/0273287 A1 | 11/2007 | Kuwahara et al. | |
| 2014/0035435 A1 | 2/2014 | Weber | |
| 2014/0210340 A1 | 7/2014 | Roberts et al. | |
| 2015/0124931 A1 | 5/2015 | Foellmer et al. | |
| 2019/0206653 A1 | 7/2019 | Zou et al. | |

FOREIGN PATENT DOCUMENTS

| | | |
|---|---|---|
| CN | 202513300 U | 10/2012 |
| CN | 106816350 A | 6/2017 |
| CN | 107432992 A | 12/2017 |
| CN | 111729212 A | 10/2020 |
| EP | 2589412 A1 | 5/2013 |
| JP | H03266344 A | 11/1991 |

OTHER PUBLICATIONS

Written Opinion in PCT/CN2021/087063 dated Jul. 1, 2021, 5 pages.

* cited by examiner

1010

1200

1300

RADIOTHERAPY DEVICE AND MICROWAVE SOURCE THEREOF

CROSS-REFERENCE TO RELATED APPLICATIONS

This application is a Continuation of International Application No. PCT/CN2021/087063, filed on Apr. 13, 2021, which claims priority of Chinese Patent Application No. 202110184055.2, filed on Feb. 10, 2021, Chinese Patent Application No. 202010731106.4, filed on Jul. 27, 2020, and Chinese Patent Application No. 202120513013.4, filed on Mar. 10, 2021, the contents of each of which are hereby incorporated by reference.

TECHNICAL FIELD

This disclosure generally relates to a radiotherapy device, and more particularly, relates to a microwave source used in the radiotherapy device.

BACKGROUND

Radiation therapy is widely used in cancer treatment and also beneficial to several other health conditions. A radiotherapy device (e.g., a linear accelerator) is often utilized to perform the radiation therapy. In such a radiotherapy device, a microwave source including an anode block and a cathode is configured to produce microwave pulses (or radio frequency pulses) for controlling the generation of radiation beams (e.g., X-rays). The microwave source is an important component for the radiotherapy device. Therefore, it is desirable to improve the design of the microwave source used in such a radiotherapy device.

SUMMARY

According to an aspect of the present disclosure, a microwave source is provided. The microwave source may include a cathode heater and a thermionic emitter. The cathode heater may include a first component, and a second component enclosing at least a portion of the first component. The thermionic emitter may be configured to release electrons when the thermionic emitter is heated by the cathode heater. At least a portion of the second component of the cathode heater may be in contact with the thermionic emitter.

In some embodiments, the at least a portion of the first component of the cathode heater may be in contact with the second component of the cathode heater.

In some embodiments, the at least a portion of the first component of the cathode heater may be embedded in the second component of the cathode heater.

In some embodiments, the first component of the cathode heater may be made of a high-melting-point and electrically conductive material.

In some embodiments, the second component of the cathode heater may be made of an electrically insulating material.

In some embodiments, the cathode heater may include a third component. The first component and the second component may be disposed between the third component and the thermionic emitter.

In some embodiments, the cathode heater may include at least one fourth component configured to increase a structural stability of the third component.

In some embodiments, the first component may be a double helix filament including a first filament and a second filament. When the first filament and the second filament are disposed in a magnetic field and powered by a power source, a first direction of a first current flow in the first filament may be opposite to a second direction of a second current flow in the second filament such that a first force on the first filament due to the magnetic field is in line with and in an opposite direction to a second force on the second filament due to the magnetic field.

In some embodiments, a first current value of the first current flow of the first filament and a second current value of the second current flow of the second filament may be equal.

In some embodiments, a direction of the magnetic field may be parallel to a filament axis direction of the double helix filament.

In some embodiments, a first diameter of the first filament may be less than a second diameter of the second filament along a direction perpendicular to the filament axis direction of the double helix filament.

In some embodiments, the first component may include one or more filaments. Each filament of the one or more filaments may be in a cylindrical configuration. When the first component is disposed in a magnetic field, a direction of the magnetic field may be parallel to an extending direction of the each filament of the one or more filaments.

In some embodiments, the first component may include a plurality of filaments arranged in a cage configuration.

In some embodiments, the microwave source may include a first connection member operably connected to a first end of the first component; and a second connection member operably connected to a second end of the first component. The first component may be powered by a power source via the first connection member and the second connection member.

In some embodiments, the thermionic emitter may include a substrate component and an electron emission layer. The cathode heater may be disposed inside the substrate component. The electron emission layer may be disposed on an outer wall of the substrate component that includes at least one discontinuity.

In some embodiments, the at least a portion of the second component of the cathode heater may be in contact with the substrate component.

In some embodiments, the electron emission layer may include at least one groove configured to cause the at least one discontinuity in the electron emission layer.

In some embodiments, the at least one groove may extend along an axial direction or a circumferential direction of the substrate component.

In some embodiments, the electron emission layer may include a plurality of grooves. The plurality of grooves may extend in a parallel direction and be equispaced.

In some embodiments, a cross section of one of the at least one groove may be rectangular, trapezoidal, or parallelogram.

In some embodiments, each of the at least one groove may include a side surface. The side surface and a surface of the electron emission layer may be arranged at an angle.

In some embodiments, the electron emission layer may include at least one first groove and at least one second groove. A first extending direction of the at least one first groove may be different from a second extending direction of the at least one second groove.

In some embodiments, the thermionic emitter further may include a filling layer disposed in the at least one groove.

In some embodiments, the substrate component may be of a cylindrical configuration.

In some embodiments, the substrate component may be made of molybdenum.

According to an aspect of the present disclosure, a microwave source is provided. The microwave source may include a cathode heater and a thermionic emitter. The cathode heater may include a double helix filament. The double helix filament may include a first filament and a second filament. The thermionic emitter may be configured to release electrons when the thermionic emitter is heated by the cathode heater. When the first filament and the second filament are disposed in a magnetic field and powered by a power source, a first direction of a first current flow in the first filament may be opposite to a second direction of a second current flow in the second filament such that a first force on the first filament due to the magnetic field is in line with and in an opposite direction to a second force on the second filament due to the magnetic field.

In some embodiments, a first current value of the first current flow of the first filament and a second current value of the second current flow of the second filament may be equal.

In some embodiments, a direction of the magnetic field may be parallel to a filament axis direction of the double helix filament.

In some embodiments, a first diameter of the first filament may be less than a second diameter of the second filament along a direction perpendicular to the filament axis direction of the double helix filament.

In some embodiments, the cathode heater may further include a supporting component in which at least a portion of the first filament or the second filament are embedded.

In some embodiments, the supporting component may be made of an electrically insulating material.

In some embodiments, the first filament and the second filament may be integrated into a single filament.

In some embodiments, the first filament and the second filament may be two separate filaments.

According to an aspect of the present disclosure, a microwave source is provided. The microwave source may include a cathode heater and a thermionic emitter. The cathode heater may include one or more filaments. Each filament of the one or more filaments may be of a cylindrical configuration. Thermionic emitter may be configured to release electrons when the thermionic emitter is heated by the cathode heater. When the cathode heater is disposed in a magnetic field, a direction of the magnetic field may be parallel to an extending direction of the each filament of the one or more filaments.

In some embodiments, the cathode heater may include a plurality of filaments arranged in a cage configuration.

In some embodiments, the microwave source may include a first connection member operably connected to a first end of the cathode heater, and a second connection member operably connected to a second end of the cathode heater. The cathode heater may be powered by a power source via the first connection member and the second connection member.

In some embodiments, the cathode heater may include a supporting component in which at least a portion of the first filament or the second filament are embedded.

In some embodiments, the supporting component may be made of an electrically insulating material.

According to an aspect of the present disclosure, a microwave source is provided. The microwave source may include a cathode heater and a thermionic emitter. The thermionic emitter may be configured to release electrons when the thermionic emitter is heated by the cathode heater. The thermionic emitter may include a substrate component and an electron emission layer. The cathode heater may be disposed inside the substrate component. The electron emission layer may be disposed on an outer wall of the substrate component. The electron emission layer may include at least one discontinuity.

In some embodiments, the electron emission layer may include at least one groove configured to cause the at least one discontinuity in the electron emission layer.

In some embodiments, the at least one groove may extend along an axial direction or a circumferential direction of the substrate component.

In some embodiments, the electron emission layer may include a plurality of grooves. The plurality of grooves may extend in a parallel direction and be equispaced.

In some embodiments, a cross section of one of the at least one groove may be rectangular, trapezoidal, or parallelogram.

In some embodiments, each of the at least one groove may include a side surface, and the side surface and a surface of the electron emission layer are arranged at an angle.

In some embodiments, the electron emission layer may include at least one first groove and at least one second groove. A first extending direction of the at least one first groove may be different from a second extending direction of the at least one second groove.

In some embodiments, the thermionic emitter may further include a filling layer disposed in the at least one groove.

In some embodiments, the substrate component may be of a cylindrical configuration.

In some embodiments, the substrate component may be made of molybdenum.

According to an aspect of the present disclosure, a radiotherapy device is provided. The radiotherapy device may include a linear accelerator. The linear accelerator may include an electron generator configured to emit electrons along a beam path, and a microwave source configured to generate microwaves. The microwave source may include an anode block and a cathode centered in the anode block. The cathode may include a cathode heater and a thermionic emitter. The cathode heater may include a first component, and a second component enclosing at least a portion of the first component. The thermionic emitter may be configured to release electrons when the thermionic emitter is heated by the cathode heater. At least a portion of the second component of the cathode heater may be in contact with the thermionic emitter.

According to an aspect of the present disclosure, a radiotherapy device is provided. The radiotherapy device may include a linear accelerator. The linear accelerator may include an electron generator configured to emit electrons along a beam path, and a microwave source configured to generate microwaves. The microwave source may include an anode block and a cathode centered in the anode block. The cathode may include a cathode heater and a thermionic emitter. The cathode heater may include a double helix filament. The double helix filament may include a first filament and a second filament. The thermionic emitter may be configured to release electrons when the thermionic emitter is heated by the cathode heater. When the first filament and the second filament are disposed in a magnetic field and powered by a power source, a first direction of a first current flow in the first filament may be opposite to a second direction of a second current flow in the second filament such that a first force on the first filament due to the magnetic field is in line with and in an opposite direction to a second force on the second filament due to the magnetic field.

According to an aspect of the present disclosure, a radiotherapy device is provided. The radiotherapy device may include a linear accelerator. The linear accelerator may include an electron generator configured to emit electrons along a beam path, and a microwave source configured to generate microwaves. The microwave source may include an anode block and a cathode centered in the anode block. The cathode may include a cathode heater and a thermionic emitter. The cathode heater may include one or more filaments. Each filament of the one or more filaments may be of a cylindrical configuration. Thermionic emitter may be configured to release electrons when the thermionic emitter is heated by the cathode heater. When the cathode heater is disposed in a magnetic field, a direction of the magnetic field may be parallel to an extending direction of the each filament of the one or more filaments.

According to an aspect of the present disclosure, a radiotherapy device is provided. The radiotherapy device may include a linear accelerator. The linear accelerator may include an electron generator configured to emit electrons along a beam path, and a microwave source configured to generate microwaves. The microwave source may include an anode block and a cathode centered in the anode block. The cathode may include a cathode heater and a thermionic emitter. The thermionic emitter may be configured to release electrons when the thermionic emitter is heated by the cathode heater. The thermionic emitter may include a substrate component and an electron emission layer. The cathode heater may be disposed inside the substrate component. The electron emission layer may be disposed on an outer wall of the substrate component. The electron emission layer may include at least one discontinuity.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
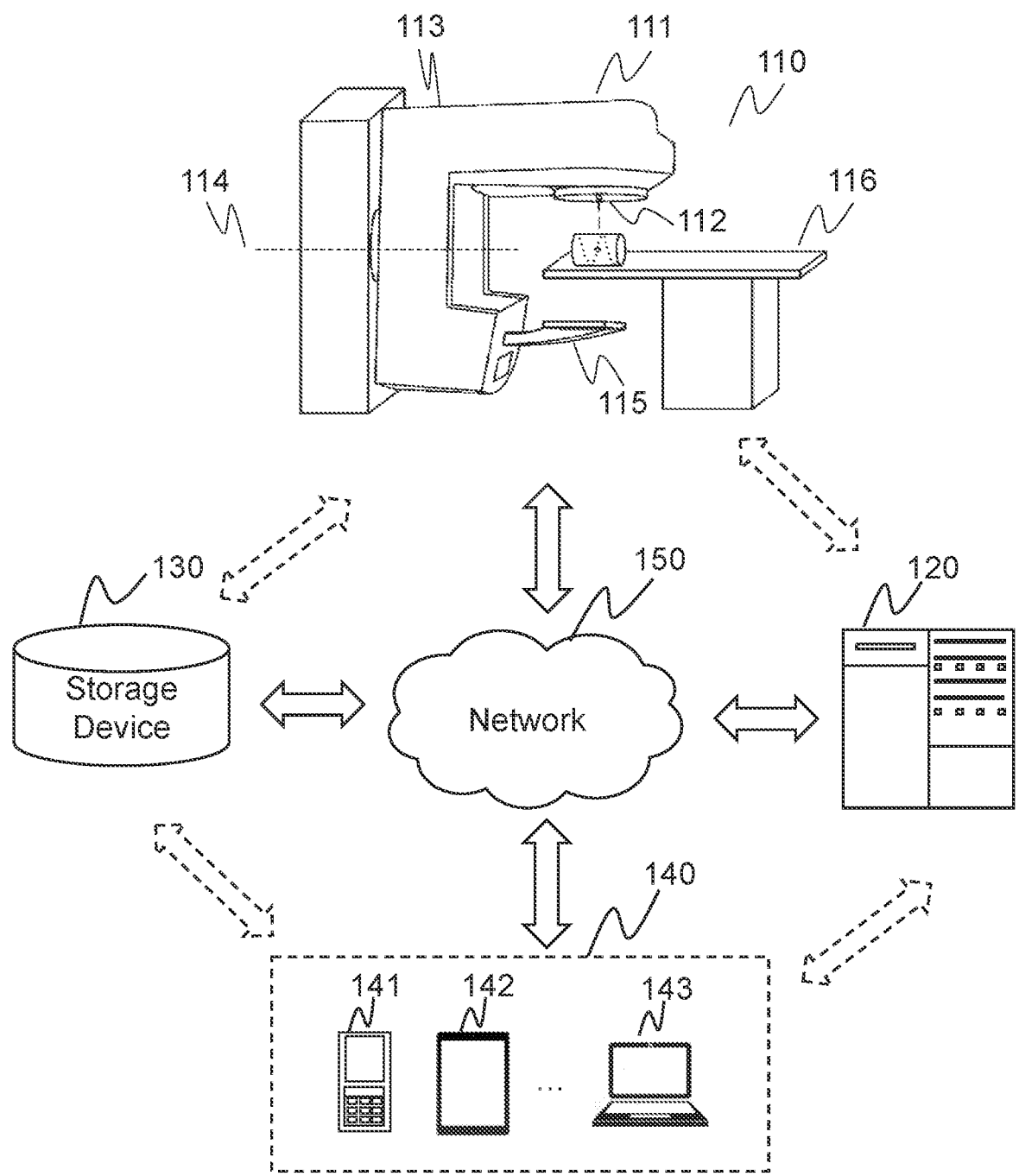
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The following description is provided with reference to exemplary embodiments that a medical device includes a microwave source (e.g., a magnetron) unless otherwise stated. However, it is understood that it is for illustration purposes only and not intended to limit the scope of the present disclosure. The microwave source disclosed herein may be suitable for other applications (e.g., a microwave oven, a particle accelerator, etc.). Merely by way of example, the medical device may include a radiotherapy device, such as an image-guided radiotherapy (IGRT) device. The IGRT device may include an imaging component (e.g., an MRI device, a PET device, a CT device) and a radiation therapy component (e.g., a linear accelerator).

An aspect of the present disclosure relates to a microwave source. The microwave source may include a cathode heater and a thermionic emitter. The cathode heater may include a first component (e.g., at least one filament), and a second component enclosing at least a portion of the first component. For example, the at least a portion of the first component of the cathode heater may be embedded in the second component of the cathode heater. The thermionic emitter may be configured to release electrons when the thermionic emitter is heated by the cathode heater. At least a portion of the second component of the cathode heater may be in contact with the thermionic emitter.

Accordingly, the heat generated by the first component may be transferred to the second component, and then the heat may be transferred from the second component to the thermionic emitter. The heat loss in the heat transfer between the first component and the second component, and the heat loss in the heat transfer between the second component and the thermionic emitter may be relatively small due to the contact between the first component and the second component and the contact between the second component and the thermionic emitter, and the heat transfer efficiency may be relatively high. The volatilization rate of the material of the first component may be reduced, and the stability of the first component may be improved. Furthermore, the second component may limit (e.g., fix) the first component, which may effectively prevent the first component from moving.

In some embodiments, the cathode heater may include multiple filaments. The filaments may be arranged such that when the filaments are powered and placed in a magnetic field, the forces (e.g., electromagnetic forces) on the filaments are reduced or counterbalanced to reduce or avoid deformation of the filaments of the cathode heater, thereby prolonging the service life of the cathode heater and reduce or avoid the energy consumption caused by the existence of the forces. For instance, the cathode heater may include a double helix filament. The double helix filament may include a first filament and a second filament. When the first filament and the second filament are disposed in a magnetic field and powered by a power source, a first direction of a first current flow of the first filament may be opposite to a second direction of a second current flow of the second filament, such that a first force on the first filament due to the magnetic field is in line with and in an opposite direction to a second force on the second filament due to the magnetic field. In some embodiments, a first current value of the first current flow of the first filament and a second current value of the second current flow of the second filament may be equal. Accordingly, the first force on the first filament and the second force on the second filament may be (substantially) counterbalanced, which may reduce or avoid the deformation and/or prolong the service life of the cathode heater. Moreover, the energy consumption caused by the existence of the forces may be reduced or avoided.

As another example, the cathode heater may include a plurality of filaments. Each filament of the plurality of filaments may be of a cylindrical configuration. The plurality of filaments may be arranged in a cage configuration. When the plurality of filaments are disposed in a magnetic field and powered by a power source, a direction of a current flow of each filament of the plurality of filaments may be (substantially) parallel to a direction of the magnetic field such that the each filament is not subjected to a force due to the magnetic field, which may reduce or avoid the deformation and/or prolong the service life of the cathode heater. Moreover, the energy consumption caused by the existence of the forces may be reduced or avoided.

In some embodiments, the thermionic emitter may include a substrate component and an electron emission layer. The cathode heater may be disposed inside the substrate component. The electron emission layer may be disposed on an outer wall of the substrate component. The electron emission layer may include at least one discontinuity (e.g., at least one groove). Accordingly, the at least one discontinuity may provide a space for accommodating a deformation of the electron emission layer due to thermal expansion and contraction. The surface stress caused by the thermal expansion or an uneven surface temperature distribution of the electron emission layer may be alleviated by the at least one discontinuity. The risk of cracking of the electron emission layer may be reduced, and the electron emission efficiency of the thermionic emitter may be improved. The service life of the thermionic emitter may be prolonged.

Another aspect of the present disclosure relates to a radiotherapy device including a linear accelerator. The linear accelerator may include an electron generator and a microwave source. The electron generator may be configured to emit electrons. The microwave source may be configured to generate microwaves. The microwave source may include a cathode heater, a thermionic emitter, and an anode block, as described elsewhere in the present disclosure. Accordingly, the working stability of the radiotherapy device may be improved, and the service life of the radiotherapy device may be prolonged.

FIG. 1 is a schematic diagram illustrating an exemplary medical system according to some embodiments of the present disclosure. As illustrated, a medical system 100 may include a medical device 110, a processing device 120, a storage device 130, a terminal 140, and a network 150. The components of the medical system 100 may be connected in one or more of various ways. Merely by way of example, as illustrated in FIG. 1, the medical device 110 may be connected to the processing device 120 directly as indicated by the bi-directional arrow in dotted lines linking the medical device 110 and the processing device 120, or through the network 150. As another example, the storage device 130 may be connected to the medical device 110 directly as indicated by the bi-directional arrow in dotted lines linking the medical device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

In some embodiments, the medical device 110 may be a radiotherapy device. The radiotherapy device may be configured to deliver a radiation therapy treatment for cancers and other conditions. For example, the radiotherapy device may deliver one or more radiation beams to a treatment region (e.g., a tumor) of a subject (e.g., a patient) for causing an alleviation of the subject's disease and/or symptoms. The subject may include any biological subject (e.g., a human being, an animal, a plant, or a portion thereof) and/or a non-biological subject (e.g., a phantom, structure/device to be non-destructively tested). In some embodiments, the radiotherapy device may be a conformal radiation therapy device, an image guided radiation therapy (IGRT) device, an intensity modulated radiation therapy (IMRT) device, an intensity modulated arc therapy (IMAT) device, or the like.

In some embodiments, the medical device 110 may include a linear accelerator (also referred to as "linac") 111. The linac 111 may generate and emit a radiation beam (e.g., an X-ray beam) from a treatment head 112. The radiation beam may go through one or more collimators (e.g., a primary collimator and/or a multi-leaf collimator (MLC)) of certain shapes, and enter into the subject. In some embodiments, the radiation beam may include electrons, photons, or other types of radiation. In some embodiments, the energy of the radiation beam may be in the megavoltage range (e.g., >1 MeV), and may therefore be referred to as megavoltage beam. The treatment head 112 may be coupled to a gantry 113. The gantry 113 may rotate, for example, clockwise or counter-clockwise around a gantry rotation axis 114. The treatment head 112 may rotate along with the gantry 113. In some embodiments, the medical device 110 may include an imaging element 115. The imaging element 115 may receive the radiation beam that passes through the subject, and generate images of patients and/or phantoms before, during and/or after a radiation treatment or a correction process based on received radiation beam. The imaging element 115 may include an analog detector, a digital detector, or the like, or a combination thereof. The imaging element 115 may be connected to the gantry 113 in any connection means, including an extendible housing. Thus, the rotation of the gantry 113 may cause the treatment head 112 and the imaging element 115 to rotate in a coordinated manner. In some embodiments, the medical device 110 may also include a table 116. The table 116 may support the subject during a radiation treatment or imaging, and/or support a phantom during a correction process of the medical device 110. The table 116 may be adjustable to suit for different application scenarios.

The processing device 120 may process data and/or information obtained from the medical device 110, the storage device 130, and/or the terminal(s) 140. In some embodiments, the processing device 120 may perform one or more radiotherapy operations. For example, the processing device 120 may process plan data (e.g., from a treatment planning system (TPS)), and determine motion parameters that may be used to control the motions of multiple components in the medical device 110. In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the terminal(s) 140 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the medical device 110.

The storage device 130 may store data, instructions, and/or any other information. In some embodiments, the storage device 130 may store data obtained from the medical device 110, the processing device 120, and/or the terminal(s) 140. The data may include image data acquired by the processing device 120, algorithms and/or models for processing the image data, etc. For example, the storage device 130 may store an image of a subject obtained from a medical device (e.g., the medical device 110). In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140). One or more components in the medical system 100 may access the data or instructions stored in the storage device 130 via the network 150. In some embodiments, the storage device 130 may be integrated into the medical device 110.

The terminal(s) 140 may be connected to and/or communicate with the medical device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140, etc.) may communicate information and/or data with one or more other components of the medical system 100 via the network 150. For example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, two or more components of the medical system 100 may be integrated into a single component. In some embodiments, a component of the medical system 100 may be implemented on two or more sub-components. Additionally or alternatively, the medical system 100 may include one or more additional components and/or one or more components of the medical system 100 described above may be omitted.

Figure 2:
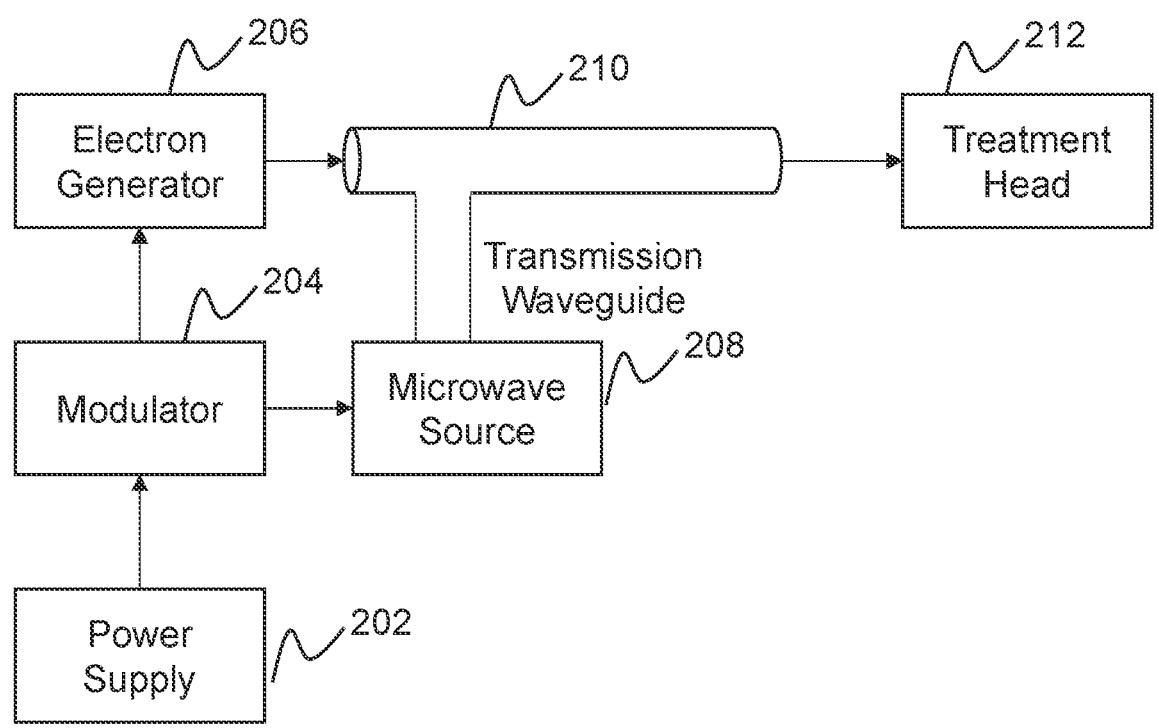
FIG. 2 is a schematic diagram illustrating exemplary components of a linear accelerator (linac) according to some embodiments of the present disclosure.

FIG. 2 is a schematic diagram illustrating exemplary components of a linear accelerator (linac) according to some embodiments of the present disclosure. In some embodiments, a linac 200 illustrated in FIG. 2 may be implemented on a radiotherapy device.

Linear Accelerators (also called "LINACS") may be widely used for a variety of tasks in a broad range of applications, including industrial applications such as non-destructive testing (NDT), security inspection (SI), radio-therapy (RT), electron beam processing-sterilization, and polymer curing. Both accelerated electron beams, and bremsstrahlung X-ray beam generated by such electron beams striking a conversion target at the end of an accelerating channel, may be used for various tasks. The type of radiation beam selected may be typically determined by the specific application and its requirements. In many applications, the requirements may include energy variation and dose rate variation of the radiation beam, including broad RB energy variation, for example, from 0.5 MeV to a maximum energy, which typically does not exceed 10 MeV due to neutron production and activation problems. However, in some cases, it can reach as high as 12 MeV, 15 MeV, 20 MeV, or even higher energies.

As illustrated in FIG. 2, the linac 200 may include a power supply 202, a modulator 204, an electron generator 206, a microwave source 208, an accelerator tube 210, and a treatment head 212. In some embodiments, the power supply 202 may be configured to provide high voltages (e.g., 45 kV) required for proper modulator operation. In some embodiments, the power supply 202 may include an alternating current (AC) circuit for supplying the alternating current voltage (ACV). In some embodiments, the power supply 202 may include a direct-current (DC) circuit for supplying the direct current voltage (DCV). The modulator 204 may be configured to simultaneously provide high voltage pulses (e.g., DC pulses) to the electron generator 206 and the microwave source 208. The electron generator 206 (e.g., an electron gun, or an electron emitter) may produce electrons injected into the accelerator tube 210. For example, the electron generator 206 may produce electrons along a range of angles and emit the electrons along a beam path. The electron beam may be injected into the accelerator tube 210. The electrons in the accelerator tube 210 may be accelerated at one or more ranges of kinetic energy using microwaves at one or more ranges of frequency. The accelerated electrons may be transmitted to the treatment head 212 for generating a radiation beam. For example, the accelerated electrons may strike a target (e.g., an X-ray target) to generate the radiation beam (e.g., X-ray beam). The radiation beam may go through one or more collimators (e.g., a primary collimator and/or a multi-leaf collimator (MLC)) of certain shapes to form a collimated radiation beam. The collimated radiation beam may irradiate a subject (e.g., a lesion of a subject) to implement radiotherapy.

In some embodiments, the microwave source 208 may be configured to generate the microwaves at one or more ranges of frequency. The microwave source 208 may be deemed as an oscillator that transforms the DC pulses from the modulator 204 into microwave pulses. In some embodiments, the microwave source 208 may be a magnetron or a klystron. In some embodiments, the microwave source 208 may include a magnetron (also referred to as single-cathode magnetron) composed of one cathode and one anode block. In some embodiments, the microwave source 208 may include a magnetron (also referred to as multi-cathode magnetron) composed of multiple cathodes and one anode block. The multiple cathodes may share the same anode block. Through different arrangements of the cathode and the anode block, the microwave sources 208 may output different microwave powers.

In some embodiments, the microwave source 208 may be a magnetron. In the magnetron, the thermionic emitter may be heated by a cathode heater. The cathode heater may include at least one filament. The electrons released from the thermionic emitter may be accelerated toward the anode block by the action of pulsed DC electric field. The anode block may include a plurality of resonant cavities. In some embodiments, at least one electromagnet may be disposed surrounding the anode block. A static magnetic field may be applied perpendicular to a cross-section plane of the plurality of resonant cavities. The released electrons can move in complex spirals toward the resonant cavities due to influence of the magnetic field. A resonance effect (or the resonance phenomenon) may occur when the resonant cavities begin to resonate at a certain resonance frequency (e.g., 3000 MHz). Thus, the resonant cavities may emit microwaves. The microwaves may be transmitted to the accelerator tube 210 through a transmission waveguide. The electrons in the accelerator tube 210 may be accelerated by the microwave power. More descriptions regarding components of the microwave source may be found elsewhere in the present disclosure (e.g., FIGS. 3A-19, and the descriptions thereof).

Figure 3A:
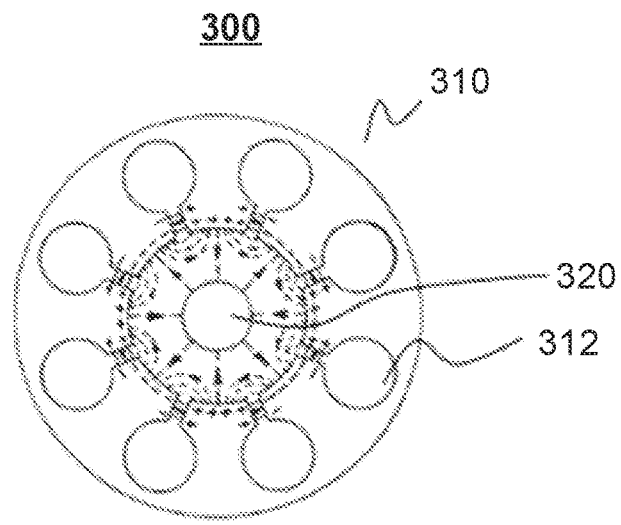
FIG. 3A illustrates a cross-sectional view of an exemplary microwave source (e.g., a magnetron) according to some embodiments of the present disclosure.

FIG. 3A illustrates a cross-sectional view of an exemplary microwave source (e.g., a magnetron) according to some embodiments of the present disclosure.

As shown in FIG. 3A, a microwave source 300 may include an anode block 310 and a cathode 320 centered in the anode block 310. The anode block 310 and the cathode 320 may be coaxial. In some embodiments, the anode block 310 may be fabricated into a cylindrical metal block (e.g., a copper block). The anode block 310 may include a plurality of resonant cavities 312. For different microwave sources, the number of the resonant cavities may be different. In some embodiments, the number of the resonant cavities may be from 8 to 20. Merely for illustration, the anode block 310 includes eight resonant cavities 312, that are, eight cylindrical holes around the cathode 320. An interaction space may be formed between the anode block 310 and the cathode 320, such as an open space between the anode block 310 and the cathode 320. In the interaction space, the electric and magnetic fields interact to exert force upon the electrons. The magnetic field is usually provided by a strong, permanent magnet mounted around the microwave source 300 so that the magnetic field is parallel with the axis of the cathode. The electrons released from the cathode 320 may travel outwardly in the interactive space. The released electrons can be accelerated toward to the anode block 310 by the action of pulsed DC electric field. The electrons may move in complex spirals towards the resonant cavities 312 due to the magnetic field. In some embodiments, the resonant cavities 312 may exist in various shapes, for example, include but not limited to a semicircular-shape cavity, a circular-shape cavity, a square-shape cavity, a rectangular-shape cavity, a fan-shape cavity, or the like, or any combination thereof.

Figure 3B:
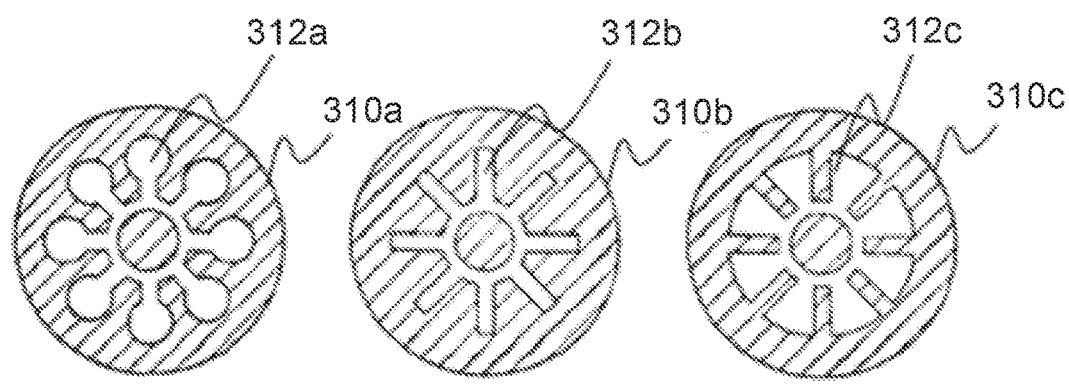
FIG. 3B illustrates different forms of an anode block in a microwave source according to some embodiments of the present disclosure.

FIG. 3B illustrates different forms of an anode block in a microwave source according to some embodiments of the present disclosure. As illustrated in FIG. 3B, an anode block 310a may include a plurality of hole-and-slot type of resonant cavities 312a, an anode block 310b may include a plurality of slot-type of resonant cavities 312b, and an anode block 310c may include a plurality of vane-type of resonant cavities 312c. The resonant cavities may be usually arranged in a radial fashion.

Figure 3C:
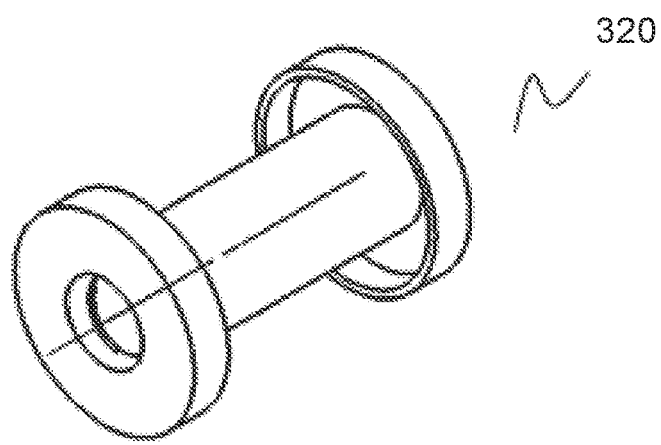
FIG. 3C illustrates an exemplary profile of a cathode of a microwave source according to some embodiments of the present disclosure.

FIG. 3C illustrates an exemplary profile of a cathode of a microwave source according to some embodiments of the present disclosure. As illustrated in FIG. 3C, the cathode 320 may include a hollow dumbbell-shape structure. In some embodiments, the cathode 320 may be made up of a hollow cylinder of emissive material (e.g., Barium oxide) surrounding a cathode heater. For example, the cathode 320 may include a cathode heater and a thermionic emitter. The cathode heater may include at least one filament. The thermionic emitter may be made up of the hollow cylinder of emissive material. When the cathode heater is heated by a power source, the outer thermionic emitter may release electrons due to a thermionic emission resulting from the heat radiation. Then the released electrons may travel outwardly in the direction of the anode block. As the electrons nip past the resonant cavities of the anode block, the energy may be passed to the resonant cavities, thus the resonant cavities may resonant at a certain resonant frequency and radiate energy in the form of microwaves.

Figure 4:
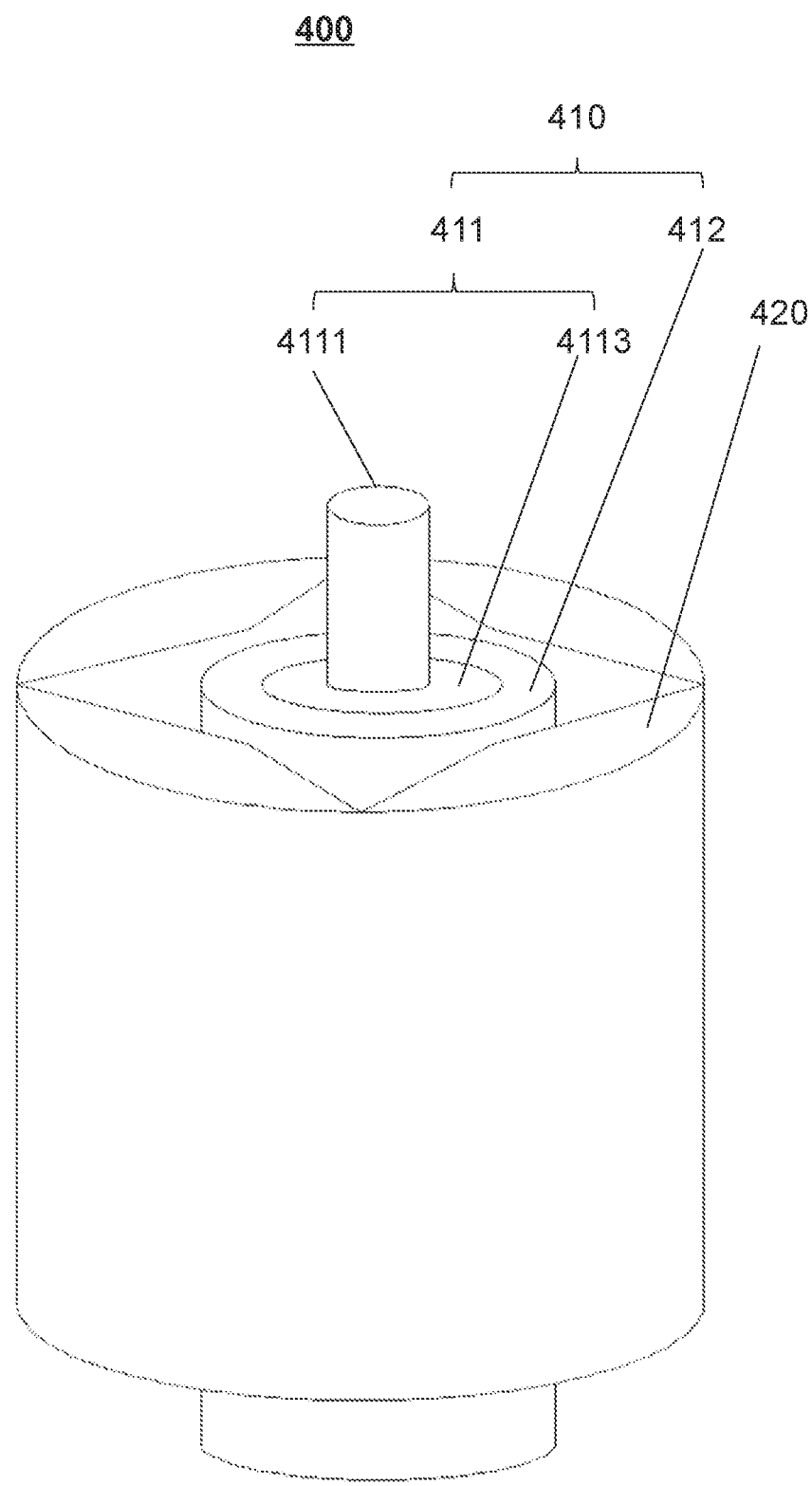
FIG. 4 is a schematic diagram illustrating an exemplary microwave source according to some embodiments of the present disclosure.

FIG. 4 is a schematic diagram illustrating an exemplary microwave source according to some embodiments of the present disclosure. As illustrated in FIG. 4, a microwave source 400 may include a cathode heater 411, a thermionic emitter 412, and an anode block 420. The cathode heater 411 and the thermionic emitter 412 collectively may also be referred to as a cathode 410.

The cathode heater 411 may be configured to heat the thermionic emitter 412. In some embodiments, the cathode heater 411 may include a first component 4111 and a second component 4113. The first component 4111 may be configured to generate heat. For example, after the first component 4111 is powered by a power source (e.g., a voltage (e.g., 20V) or a current (e.g., 15A) is applied to the first component 4111), the first component 4111 may generate heat, and the heat may be transferred from the first component 4111 to the second component 4113. The heat may then be transferred from the second component 4113 to the thermionic emitter 412.

In some embodiments, the first component 4111 may include at least one filament. The filament may be made of a high-melting-point (e.g., >2000 QC) and electrically conductive material. Exemplary materials of the first component 4111 may include tungsten, molybdenum, rhenium, an alloy thereof (e.g., a tungsten-rhenium alloy), or the like, or any combination thereof. Merely by way of example, the first component 4111 may be made of a tungsten-rhenium alloy. Since the tungsten-rhenium alloy has a relatively high melting point, the first component 4111 made of the tungsten-rhenium alloy may tolerate a high temperature, undergoing little or no deformation and/or volatilization at the high temperature.

In some embodiments, the first component 4111 may include a single helix filament (e.g., a first component 5111 illustrated in FIG. 5), a double helix filament (e.g., a double helix filament 1000 illustrated in FIGS. 10A, 10B and 11), one or more filaments of a columnar configuration (e.g., a cylindrical configuration) (e.g., a first component 4111 illustrated in FIG. 4, a first component 8111 illustrated in FIGS. 8A, 8B, 9A, and 9B), a plurality of filaments arranged in a cage configuration (e.g., a plurality of filaments 1210 illustrated in FIGS. 12A, and 12B), or the like. For example, as illustrated in FIG. 4, the first component 4111 may include a filament of a cylindrical configuration. More descriptions of the filament may be found elsewhere in the present disclosure (e.g., FIGS. 10A-13C, and descriptions thereof). In some embodiments, a cross section of the filament may be circular, rectangular, trapezoidal, elliptical, etc.

The second component 4113 may be configured to electrically insulate the first component 4111 from the thermionic emitter 412. In some embodiments, the second component 4113 may have a cylindrical shape, a conical shape, a rectangular shape, a spiral shape, or the like. In some embodiments, the second component 4113 may be made of a high temperature resistant and electrically insulating material. Exemplary materials of the second component 4113 may include ceramic materials, mica materials, or the like, or any combination thereof. Exemplary ceramic materials may include oxide ceramics (e.g., alumina ceramics), nitride ceramics (e.g., silicon nitride ceramics), carbide ceramics (e.g., silicon carbide ceramics), or the like. Merely by way of example, the second component 4113 may be made of a ceramic material. The ceramic material may have a desirable thermal conductivity such that the second component 4113 can conduct the heat emitted by the first component 4111 to the thermionic emitter 412 efficiently to avoid or minimize heat accumulation in the first component 4111. Therefore, the stability of the first component 4111 may be improved. In addition, the ceramic material may have a desirable strength and high temperature resistance, which may ensure the stability of the cathode heater 411 during operation.

In some embodiments, the second component 4113 may enclose at least a portion of the first component 4111. As used herein, "a component B enclosing a component A" refers to that the component B surrounds the component A such that the component A is separated from other components, e.g., the component A not touching or in contact with a component other than the component B. In some embodiments, the at least a portion of the first component 4111 may be in contact with the second component 4113. For example, as illustrated in FIG. 4, at least a portion of the first component 4111 may be embedded in the second component 4113, and the first component 4111 is not in contact with the thermionic emitter 412. The heat generated by the first component 4111 may be transferred to the second component 4113 efficiently to avoid or minimize heat accumulation in the first component 4111. The heat loss in the heat transfer between the first component 4111 and the second component 4113 may be relatively small, and the heat transfer efficiency may be relatively high. Since the first component 4111 is embedded in the second component 4113, the volatilization rate of the material of the first component 4111 may be reduced, and the stability of the first component 4111 may be improved. Furthermore, the second component 4113 may provide mechanical support for (e.g., fix) the first component 4111, which may effectively prevent the first component 4111 from moving.

The thermionic emitter 412 may be configured to release electrons when the thermionic emitter 412 is heated by the cathode heater 411. For example, when the cathode heater 411 is heated by a power source, the thermionic emitter 412 may release electrons due to a thermionic emission resulting from thermal radiation. Then the released electrons may travel outwardly in the direction of the anode block 420, as described elsewhere in the present disclosure (e.g., FIGS. 2, 3, and the descriptions thereof).

In some embodiments, the thermionic emitter 412 may be made of metal. Exemplary metals may include tungsten, molybdenum, or the like. In some embodiments, a thermionic emission material may be coated on a surface of the thermionic emitter 412. Exemplary thermionic emitter materials may include nickel, molybdenum, or the like, or an alloy thereof. Exemplary thermionic emission materials may include alkaline earth metal oxides, or the like. In some embodiments, the thermionic emitter 412 may have a porous structure (e.g., a honeycomb structure). The thermionic emission material may be filled in a plurality of pores of the thermionic emitter 412. Exemplary thermionic emitter materials may include molybdenum, tungsten, a tungsten-iridium alloy, a tungsten-osmium alloy, or the like, or any combination thereof. Exemplary thermionic emission materials may include alkaline earth metal aluminate, scandate, or the like, or any combination thereof. When external heat energy is applied to the thermionic emission material so that the thermal energy input to a charge carrier overcomes the work function of the thermionic emission material, electrons may be emitted from the surface of the thermionic emission material. The thermionic emitter 412 may have any suitable shape. For example, the thermionic emitter 412 may have the shape of a hollow cylinder with a cavity. The cathode heater 411 may be disposed in the cavity of the thermionic emitter 412.

Figure 6:
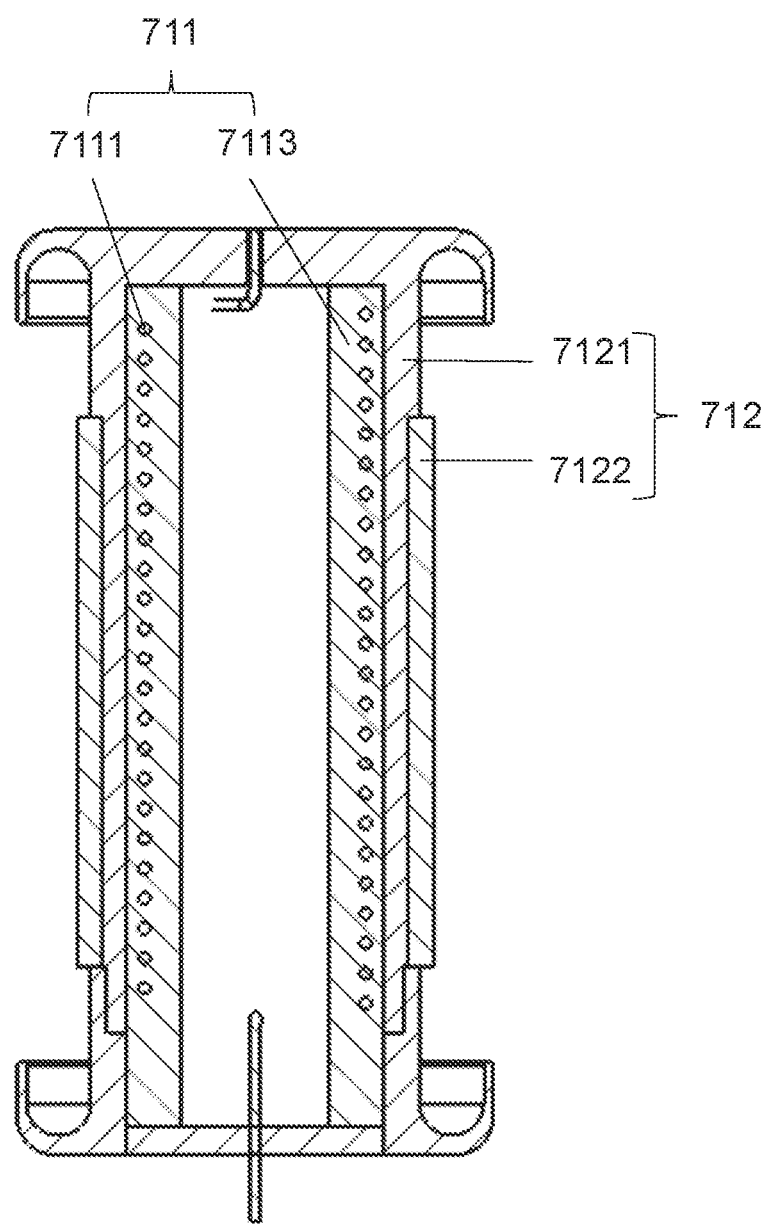
FIG. 6 is an axial sectional view of an exemplary cathode according to some embodiments of the present disclosure.
Figure 7:
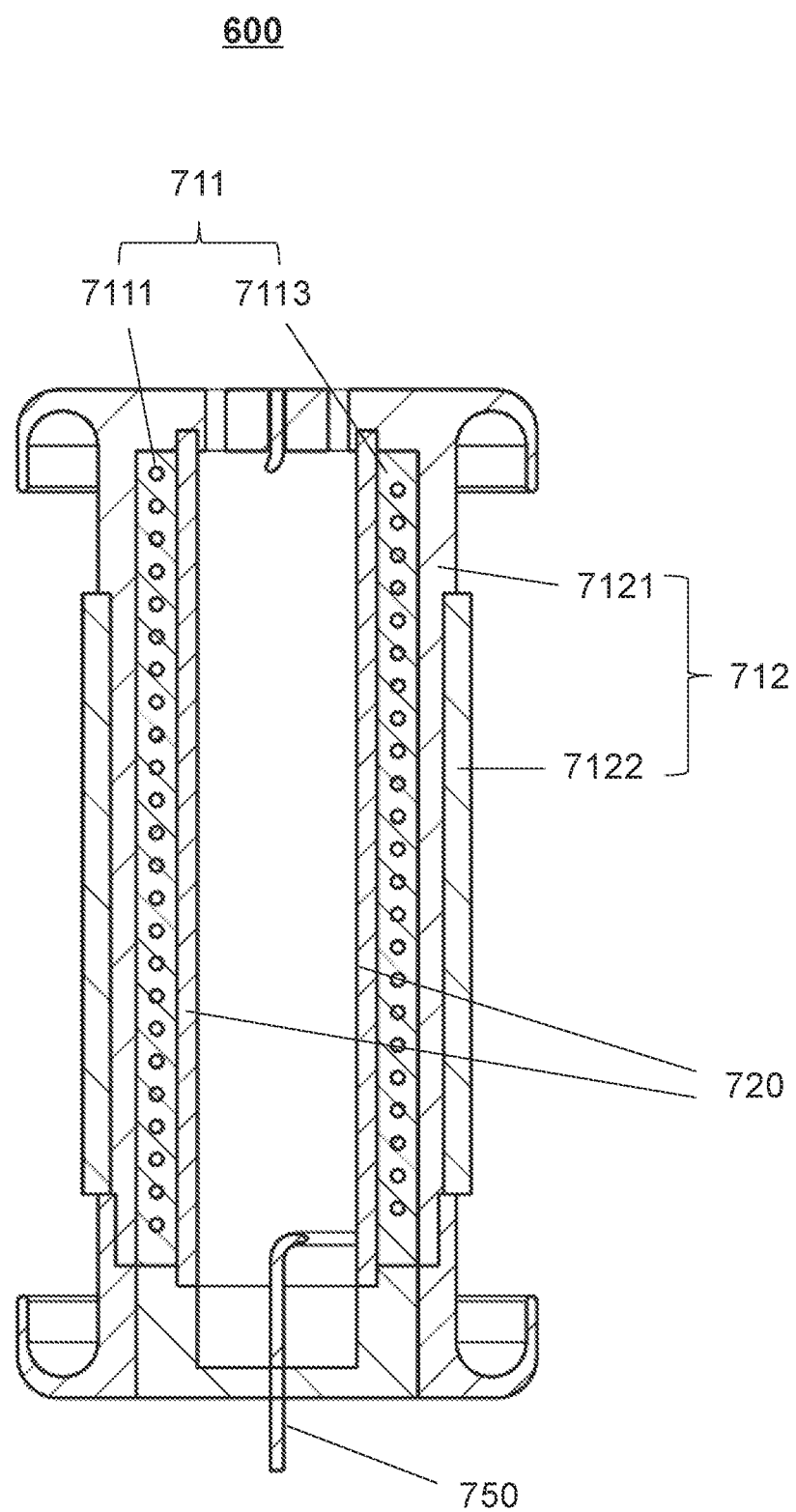
FIG. 7 is an axial sectional view of an exemplary cathode according to some embodiments of the present disclosure.
Figure 14:
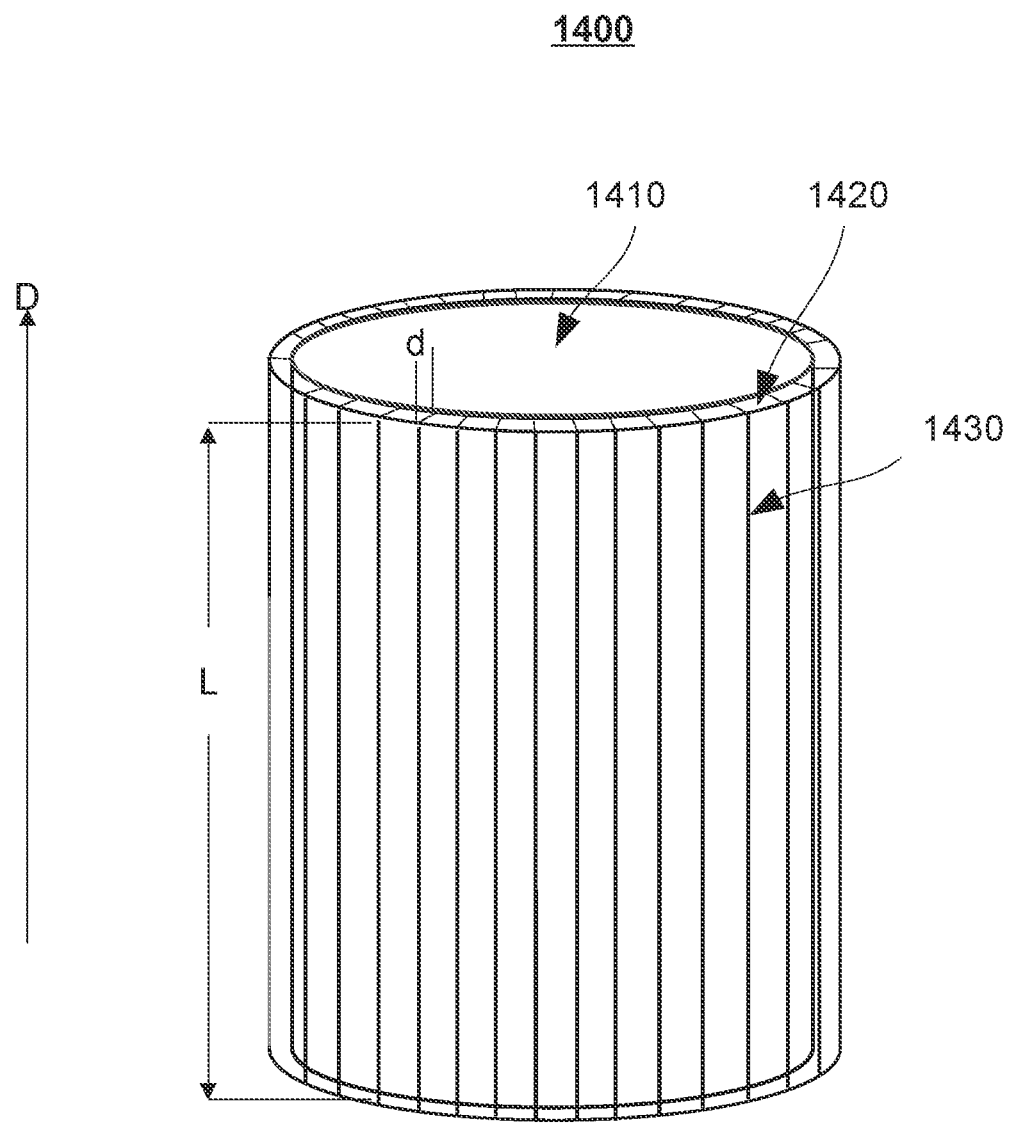
FIG. 14 is a schematic diagram illustrating an exemplary thermionic emitter according to some embodiments of the present disclosure.

In some embodiment, the thermionic emitter 412 may include a substrate component (e.g., a substrate component 7121 illustrated in FIGS. 6-7, a substrate component 8121 illustrated in FIGS. 8A, 8B, 9A, and 9B, a substrate component 1410 illustrated in FIG. 14), and an electron emission layer (e.g., an electron emission layer 7122 illustrated in FIGS. 6-7, an electron emission layer 8122 illustrated in FIGS. 8A, 8B, 9A, and 9B, an electron emission layer 1420 illustrated in FIG. 14). More descriptions of the substrate component and the electron emission layer may be found elsewhere in the present disclosure (e.g., FIGS. 14-17C, and the descriptions thereof).

In some embodiments, at least a portion of the second component 4113 may be in contact with the thermionic emitter 412. For example, the at least a portion of the second component 4113 may be in contact with the substrate component of the thermionic emitter 412.

According to some embodiments of the present disclosure, by disposing the second component 4113 between the first component 4111 and the thermionic emitter 412, the second component 4113 may facilitate the heat transfer between the first component 4111 and the thermionic emitter 412. Compared with the heat transfer between the first component 4111 and the thermionic emitter 412 via thermal radiation, the heat transfer efficiency between the first component 4111 and the thermionic emitter 412 via the second component 4113 may be relatively high.

In addition, the first component 4111 may be in contact with the second component 4113, and the second component 4113 may be in contact with the thermionic emitter 412. The temperature difference between the first component 4111 and the second component 4113, and the temperature difference between the second component 4113 and the thermionic emitter 412 may be relatively small (e.g., less than 200° C.). Therefore, the required heating temperature of the first component 4111 may be relatively low, and the voltage required to heat the first component 4111 to the required heating temperature may also be relatively low. For example, during the operation of the thermionic emitter 412, the thermionic emitter 412 needs to be maintained at a constant high temperature (e.g., 800° C., 1000° C.). In a traditional cathode, the temperature difference between the filament and a thermionic emitter may be relatively high (e.g., greater than 700° C.). That is, the required heating temperature of the filament may be higher than 1700° C. such that the thermionic emitter can be maintained at 1000° C. for operation. However, by using the cathode disclosed in the present disclosure, the required heating temperature of the filament (i.e., the first component 4111) may be around (e.g., less than) 1200° C. to maintain the temperature of the thermionic emitter at 1000° C. for operation.

The reduction of the required heating temperature of the filament may reduce the fatigue of filament material, and reduce the volatilization rate of the filament material, thereby increasing the service life of the filament. Furthermore, the filament material volatilized at high temperature may condense in a low temperature place, which may decrease the insulation performance of the second component 4113.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 5:
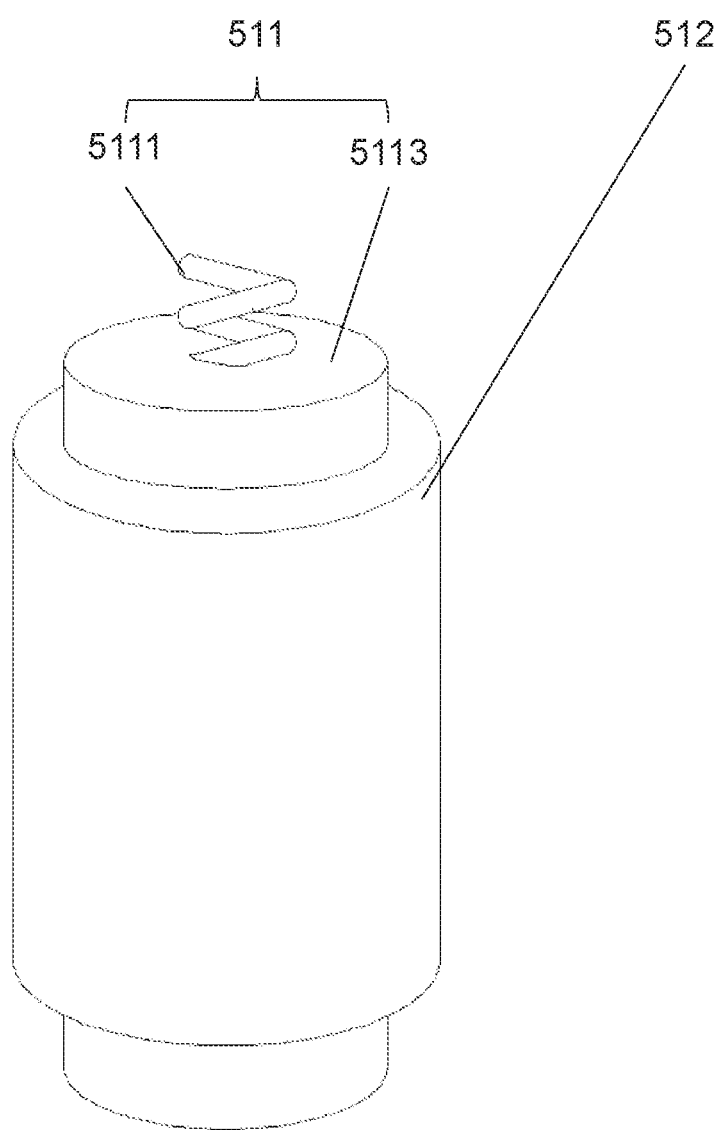
FIG. 5 is a schematic diagram illustrating an exemplary cathode according to some embodiments of the present disclosure.

FIG. 5 is a schematic diagram illustrating an exemplary cathode according to some embodiments of the present disclosure. A cathode 500 may be similar to the cathode 410, except for certain features described below.

As illustrated in FIG. 5, the cathode 500 may include a cathode heater 511 and a thermionic emitter 512. The cathode heater 511 may include a first component 5111 and a second component 5113. The first component 5111 may include a filament of a helix configuration. That is, the filament may be spirally wound to form a helix filament. Compared with a filament of a cylindrical configuration, the length of the helix filament in a limited space of the thermionic emitter 512 may be greater, the resistance of the helix filament to a current flow may be greater, and more electric energy may be generated and then converted into thermal energy. Therefore, the heating power of the helix filament may be relatively high.

At least a portion of the first component 5111 may be embedded in the second component 5113. At least a portion of the second component 5113 may be in contact with the thermionic emitter 512. The second component 5113 may be similar to the second component 4113. The thermionic emitter 512 may be similar to the thermionic emitter 412.

FIG. 6 is an axial sectional view of an exemplary cathode according to some embodiments of the present disclosure. FIG. 7 is an axial sectional view of an exemplary cathode according to some embodiments of the present disclosure.

As illustrated in FIG. 6, a cathode 600 may include a cathode heater 711 and a thermionic emitter 712. The cathode heater 711 may include a first component 7111 and a second component 7113. The first component 7111 may include a filament of a helix configuration (e.g., a single helix filament, a double helix filament). The second component 7113 may have a first cylindrical structure with a hollow cavity. At least a part of the first component 7111 may be embedded in the second component 7113. For example, the first component 7111 may be fully embedded in the second component 7113.

In some embodiment, the thermionic emitter 712 may include a substrate component 7121 and an electron emission layer 7122. The substrate component 7121 may be configured to support the electron emission layer 7122. The substrate component 7121 may be made of molybdenum, tungsten, rhenium, or the like, or any combination thereof. The electron emission layer 7122 may be configured to release electrons when the electron emission layer 7122 is heated by the cathode heater 711. In some embodiments, the electron emission layer 7122 may be disposed on an outer wall of the substrate component 7121. In some embodiments, the electron emission layer 7122 may be made of a thermionic emission material as described elsewhere in the present disclosure.

In some embodiments, the substrate component 7121 may have a second cylindrical structure with a hollow cavity. The substrate component 7121 may be disposed on the outside of the first cylindrical structure of the second component 7113. In some embodiments, at least a portion of an inner wall of the second cylindrical structure of the substrate component 7121 may be in contact with an outer wall of the first cylindrical structure of the second component 7113. For example, all of the inner wall of the second cylindrical structure of the substrate component 7121 may be in contact with the outer wall of the first cylindrical structure of the second component 7113.

In some embodiments, a difference between an outer diameter of the first cylindrical structure of the second component 7113 and an inner diameter of the second cylindrical structure of the substrate component 7121 may be less than a threshold (e.g., 0.1 mm, 0.5 mm). Accordingly, the second cylindrical structure of the substrate component 7121 may be snugly fit the first cylindrical structure of the second component 7113 so that the inner wall of the second cylindrical structure of the substrate component 7121 may be in contact with the outer wall of the first cylindrical structure of the second component 7113. More descriptions of the substrate component and the electron emission layer may be found elsewhere in the present disclosure (e.g., FIGS. 14-17C, and descriptions thereof).

According to some embodiments of the present disclosure, the first component 7111 may be embedded in the second component 7113 such that the first component 7111 may be in contact with the second component 7113. The heat generated by the first component 7111 may be transferred to the second component 7113 efficiently. The second component 7113 may be in contact with the thermionic emitter 712, and the heat may be transferred from the second component 7113 to the thermionic emitter 712 efficiently. Therefore, the efficiency of the heat transfer between the cathode heater 711 and the thermionic emitter 712 may be improved.

In addition, the required heating temperature of the first component 7111 may be relatively low, the volatilization rate of the first component 7111 may be reduced, and the stability of the first component 7111 may be improved. The service life of the first component 7111 may be prolonged. Furthermore, the second component 7113 may provide mechanical support for (e.g., fix) the first component 7111, which may effectively prevent the first component 7111 from moving.

In some embodiments, as illustrated in FIG. 7, the cathode heater 711 may include a third component 720. The third component 720 may be configured to facilitate the manufacturing of the second component 7113. The first component 7111 and the second component 7113 may be disposed between the third component 720 and the substrate component 7121 of the thermionic emitter 712. The third component 720 may be made of a high-melting-point (e.g., >2000 QC) material. Exemplary materials of the third component 720 may include tungsten, molybdenum, rhenium, or the like, or an alloy thereof, or any combination thereof. In some embodiments, the third component 720 may have a third cylindrical structure.

In some embodiments, during the manufacturing process of the cathode heater 711, the third component 720 may be supported in (e.g., one or more notches of) the cavity of the substrate component 7121. For instance, on the inner wall of the substrate component 7121 forming the cavity, there may be one or more notches configured to facilitate the positioning of the third component 720 in the cavity of the substrate component 7121. The first component 7111 of a desired shape and the material of the second component 7113 (e.g., ceramic powders) may be disposed between the third component 720 and the substrate component 7121. Then the material of the second component 7113 (e.g., ceramic powders) may be molded (e.g., sintered) to form the cathode heater 711. For example, after the third component 720 is positioned in the cavity of the substrate component 7121, a tungsten filament of a cylindrical configuration and ceramic powders may be disposed between the third component 720 and the substrate component 7121. Then the ceramic powders may be sintered to form the second component 7113. In this situation, the first component 7111 may be in contact with the second component 7113, and the efficiency of the heat transfer between the first component 7111 and the second component 7113 may be relatively high.

In some embodiments, an inner cavity (e.g., one or more holes, a cylindrical cavity, a helix cavity) that can accommodate the first component 7111 in (a wall of) the second component 7113 may be formed during the manufacturing process (e.g., molding process) of the second component 7113. After the second component 7113 is formed (e.g., molded), the first component 7111 may be disposed in the inner cavity of the second component 7113. For example, after the third component 720 is supported in the cavity of the substrate component 7121, a mold of a cylindrical configuration and ceramic powders may be disposed between the third component 720 and the substrate component 7121. Then the ceramic powders may be molded (e.g., sintered) to form the second component 7113. The mold may be taken out of the second component 7113, and a cylindrical cavity may be formed in (the wall of) the second component 7113. Then a tungsten filament of a cylindrical configuration may be placed in the cylindrical cavity of the second component 7113. In this situation, a gap between the first component 7111 and the second component 7113 may exist, which may provide room for the thermal expansion and deformation of the materials of the first component 7111 and the second component 7113.

In some embodiments, after the molding process (e.g., sintering process) of the second component 7113 is completed, the third component 720 may be disassembled from (one or more notches of) the cavity of the substrate component 7121. In this situation, the weight of the cathode 600 may be reduced, and the heating rate of the cathode 600 may be increased.

In some embodiments, after the molding process (e.g., sintering process) of the second component 7113 is completed, the third component 720 may remain in the cavity of the substrate component 7121. For example, before the molding process (e.g., sintering process) of the second component 7113 and after the third component 720 is positioned in the cavity of the substrate component 7121 via one or more notches on the inner wall of the substrate component 7121 that forms the cavity, a solder may be filled in the one or more notches. During the molding process (e.g., sintering process), the third component 720 may be welded to the substrate component 7121. In this situation, the configuration of the third component 720 may prevent a piece of insulating material of the second component 7113 peeled off due to thermal expansion and contraction from falling into an anode vacuum chamber through a vent hole 750.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the first component 7111 may have any shape. For example, the first component 7111 may include a plurality of filaments. Each filament may be of a cylindrical configuration, as described elsewhere in the present disclosure (e.g., FIGS. 4, 8A, 8B, 9A, 9B, 12A, 12B, 13A-13C, and descriptions thereof).

In some embodiments, the cathode heater 711 may be manufactured according to different manufacturing processes. In some embodiments, a mold may be disposed on the first component 7111, and the material of the second component 7113 (e.g., ceramic powders) may be injected into the mold. Then the material of the second component 7113 may be sintered to prepare the cathode heater 711. In some embodiments, after the cathode heater 711 is manufactured, the cathode heater 711 may be disposed inside the substrate component 7121 of the thermionic emitter 712. For example, after the cathode heater 711 is manufactured, the cathode heater 711 may be disposed between the substrate component 7121 of the thermionic emitter 712 and the third component 720.

In some embodiments, the first component 7111 may be disposed in the cavity of the first cylindrical structure of the second component 7113. For example, the first component 7111 may be in contact with the inner wall of the cavity of the second component 7113, in order to reduce the heat loss in the heat transfer between the first component 7111 and the second component 7113. As another example, the first component 7111 may be separated from, and therefore not in contact with, the inner surface of the cavity of the second component 7113, and a gap between the first component 7111 and the second component 7113 may be formed, which may provide room for the thermal expansion and deformation of the materials of the first component 7111 and the second component 7113.

Figure 8A:
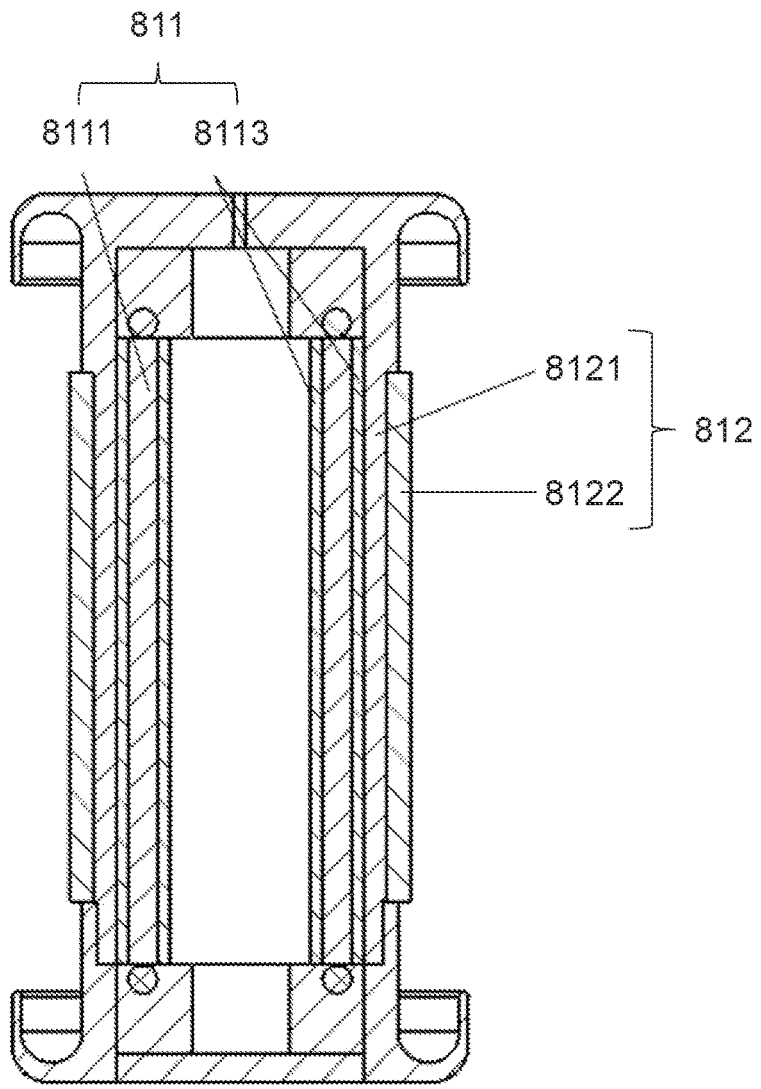
FIG. 8A is an axial sectional view of an exemplary cathode according to some embodiments of the present disclosure.
Figure 8B:
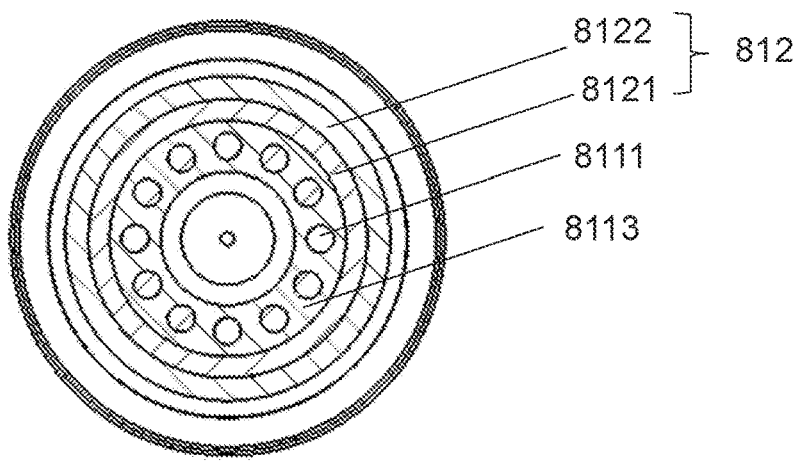
FIG. 8B is a top view of an exemplary cathode according to some embodiments of the present disclosure.
Figure 9A:
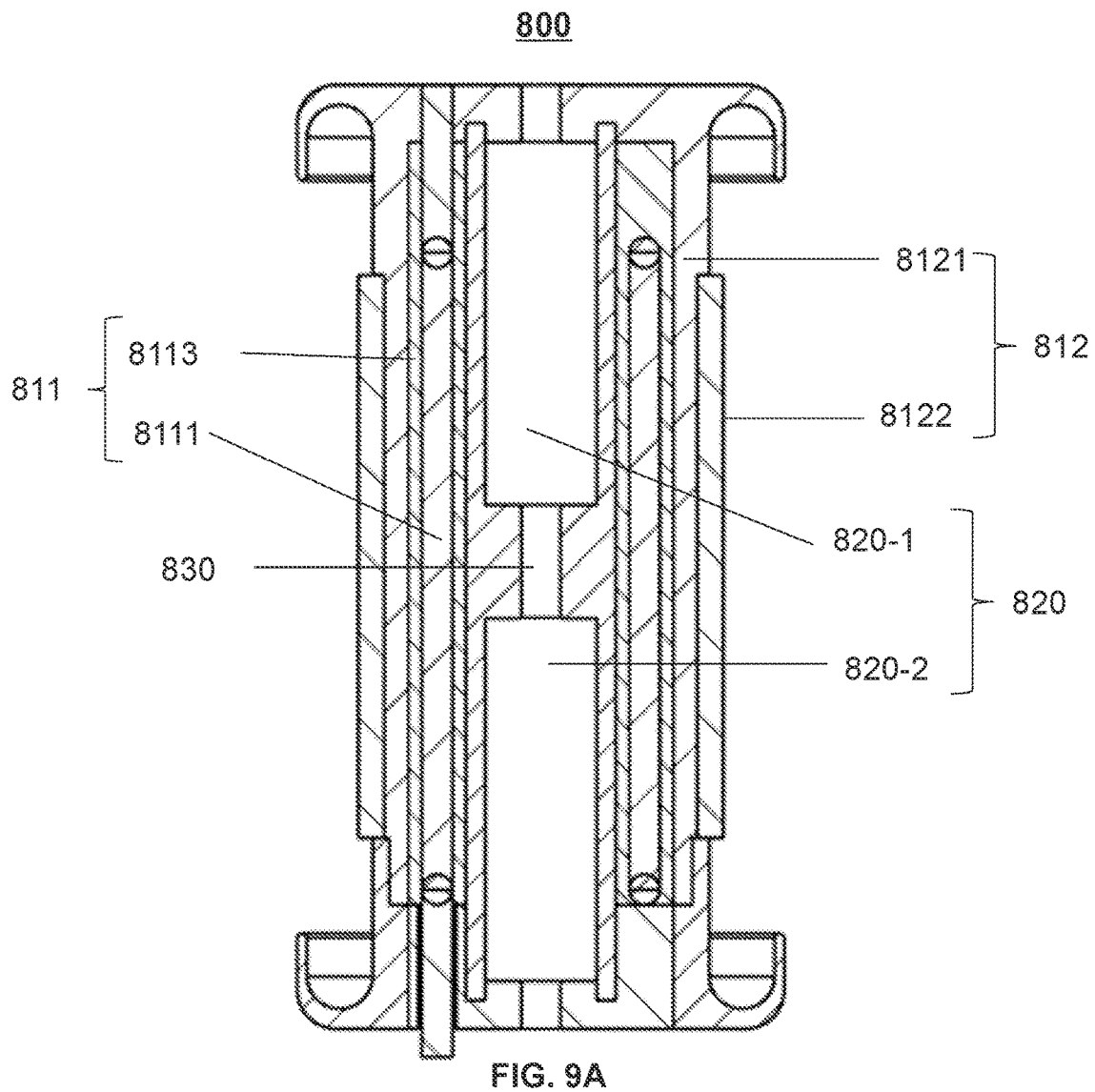
FIG. 9A is an axial sectional view of an exemplary cathode according to some embodiments of the present disclosure.
Figure 9B:
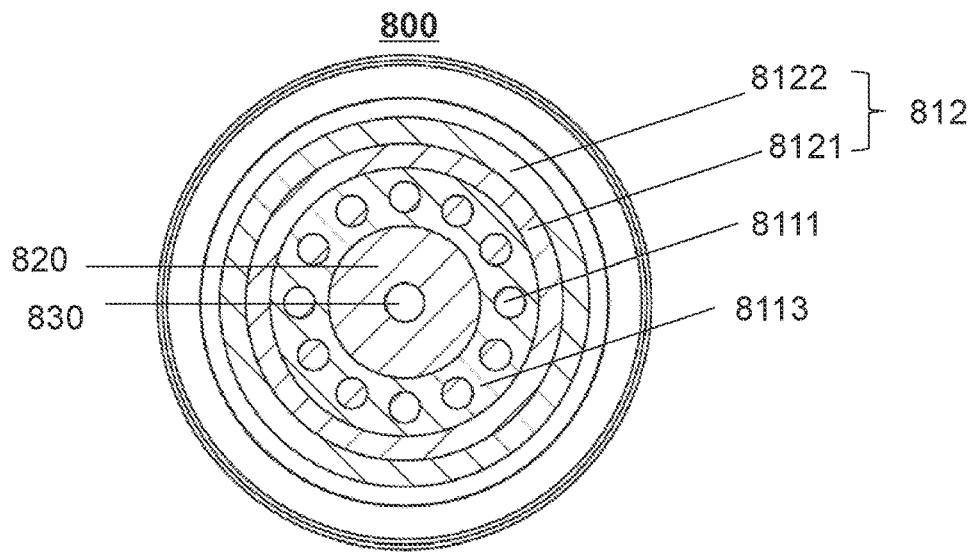
FIG. 9B is a top view of an exemplary cathode according to some embodiments of the present disclosure.

FIG. 8A is an axial sectional view of an exemplary cathode according to some embodiments of the present disclosure. FIG. 8B is a top view of an exemplary cathode according to some embodiments of the present disclosure. FIG. 9A is an axial sectional view of an exemplary cathode according to some embodiments of the present disclosure. FIG. 9B is a top view of an exemplary cathode according to some embodiments of the present disclosure. A cathode 800 may be similar to the cathode 600, except for certain features described below.

As illustrated in FIGS. 8A, and 8B, the cathode 800 may include a cathode heater 811 and a thermionic emitter 812. The cathode heater 811 may include a first component 8111 and a second component 8113. The first component 8111 may include a plurality of filaments. Each filament may be of a cylindrical configuration. The second component 8113 may have a cylindrical structure with a cavity. The plurality of filaments may be embedded in and arranged along the sidewall of the cylindrical structure of the second component 8113 as illustrated in FIG. 8B. At least a part of the first component 8111 may be embedded in the second component 8113. The thermionic emitter 812 may include a substrate component 8121 and an electron emission layer 8122. The substrate component 8121 may be similar to the substrate component 7121. The electron emission layer 8122 may be similar to the electron emission layer 7122.

In some embodiments, as illustrated in FIGS. 9A and 9B, the cathode heater 811 may include a third component 820. The third component 820 may include a plurality of chambers. For example, the third component 820 may include a first chamber 820-1 and a second chamber 820-2. The first chamber 820-1 and the second chamber 820-2 may be connected via a fourth component 830. The fourth component 830 may have any suitable structure. In some embodiments, the fourth component 830 may have a cylindrical structure. The fourth component 830 may increase the structural stability of the third component 820. For example, the fourth component 830 may prevent the third component 820 from deformation during the sintering process of the second component 8113. Merely by way of example, the fourth component 830 may have a cylindrical structure with a cavity (e.g., a cylindrical structure with a through hole). Accordingly, gas in the first chamber 820-1 and the second chamber 820-2 may be circulated via the fourth component 830, which may ensure the vacuum degree of a microwave source, and improve the performance of the microwave source. The fourth component 830 may be made of a high-melting-point (e.g., >1000 QC) material as described elsewhere in the present disclosure.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the third component 820 and/or the fourth component 830 may be omitted. In some embodiments, the third component 820 may have a similar structure to the third component 720 illustrated in FIG. 7. In some embodiments, the third component 720 may have a similar structure to the third component 820 illustrated in FIG. 8. In some embodiments, the first component 8111 may have any shape. For example, the first component 8111 may include a filament of a helix configuration (e.g., a single helix filament, a double helix filament) as described elsewhere in the present disclosure.

Figure 10A:
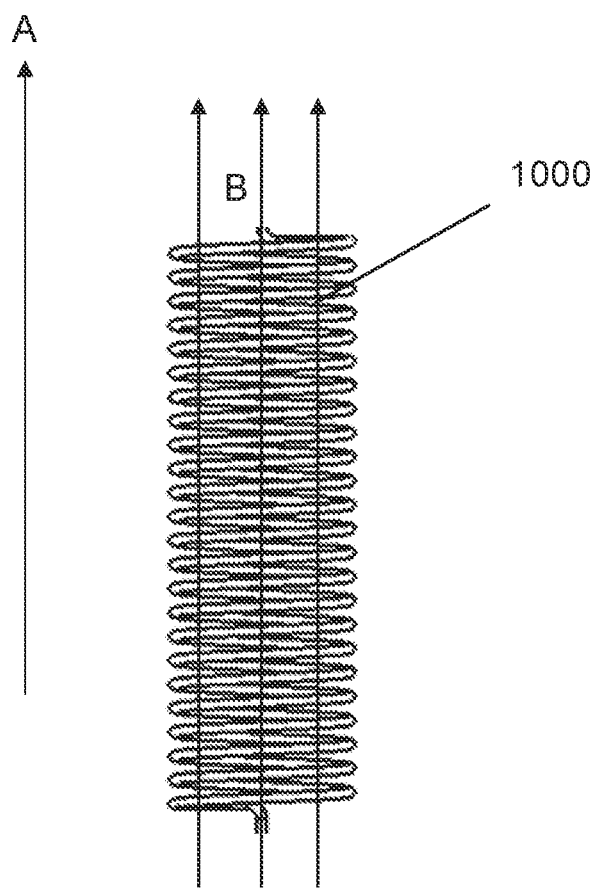
FIGS. 10A and 10B are a schematic diagram illustrating an exemplary cathode heater according to some embodiments of the present disclosure.
Figure 10B:
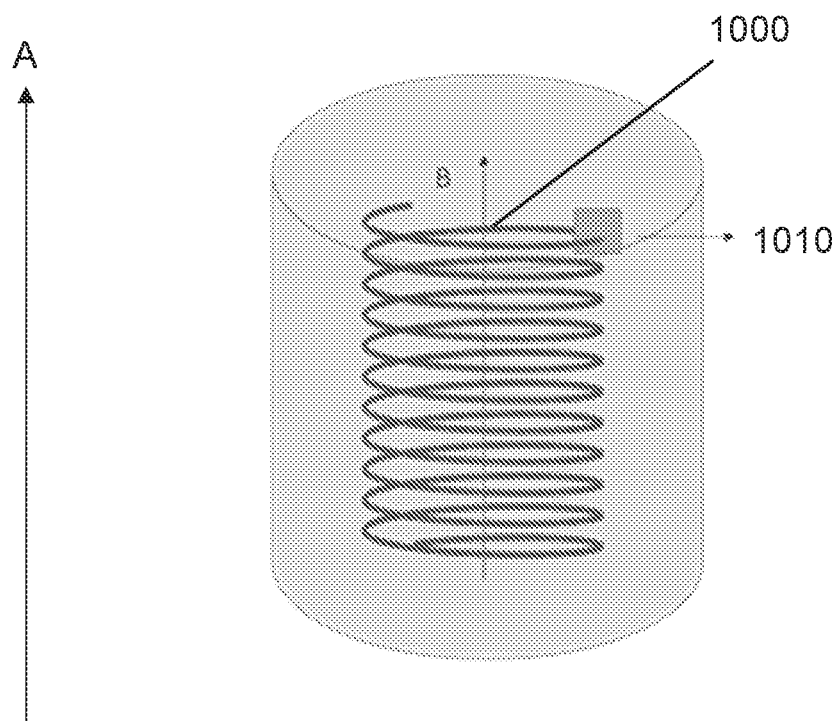

FIGS. 10A and 10B are a schematic diagram illustrating an exemplary cathode heater according to some embodiments of the present disclosure.

As illustrated in FIGS. 10A and 10B, a cathode heater may include a double helix filament 1000. The double helix filament 1000 may be disposed in a magnetic field B. In some embodiments, the magnetic field B may be generated by a microwave source as described in FIG. 3. The magnetic field B may be of a certain strength and direction. In some embodiments, a direction of the magnetic field B may be (substantially) parallel to a filament axis direction A of the double helix filament 1000. As used herein, a filament axis direction of a double helix filament refers to an extension direction of the double helix filament. As used herein, "substantially" indicates that the deviation is below a threshold (e.g., 5%, 10%, 15%, 20%, 30%, etc.). For instance, a direction being substantially parallel to an axis (or another direction) indicates that the deviation of the angle between the direction and the axis (or the other direction) from zero degrees is below a threshold. Merely by way of example, a direction being substantially parallel to an axis (or another direction) indicates that the angle between the direction and the axis (or the other direction) is below 30°, or below 25°, or below 20°, or below 15°, or below 10°, or below 5°, etc. In some embodiments, the direction of the magnetic field B may have an angle (e.g., 10°, 15°, 30°) with the filament axis direction A.

Figure 11:
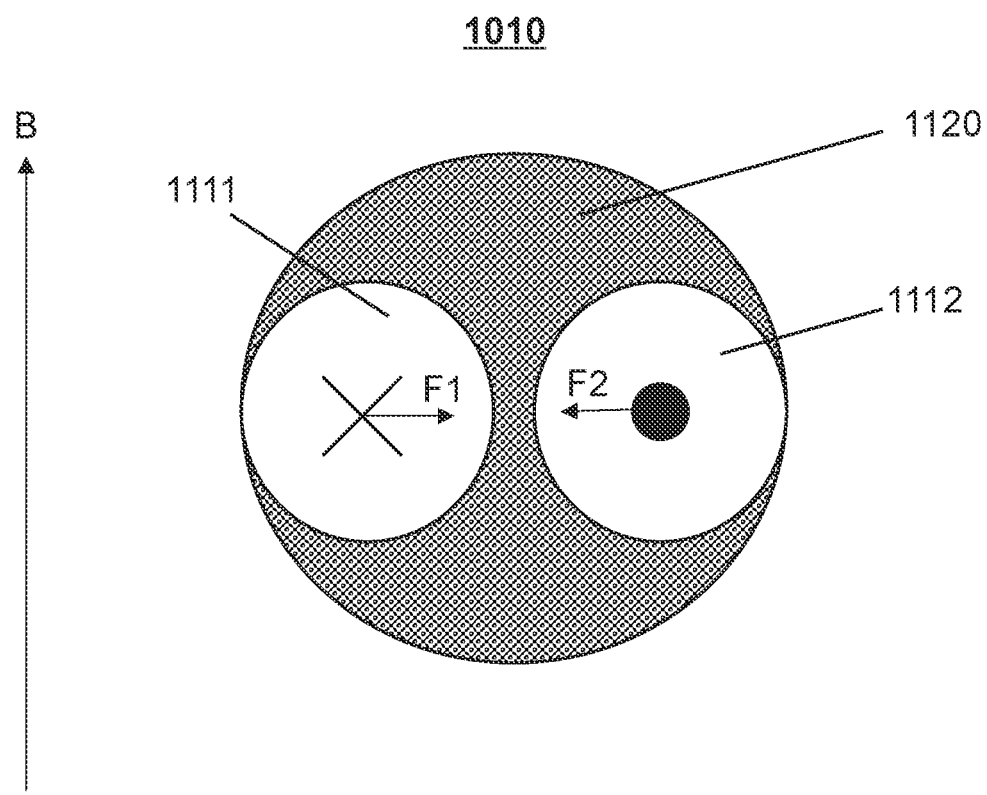
FIG. 11 is an enlarged view of a cross-sectional region 1010 of the double helix filament 1000 shown in FIG. 10B according to some embodiments of the present disclosure.

FIG. 11 is an enlarged view of a cross-sectional region 1010 of the double helix filament 1000 shown in FIG. 10B according to some embodiments of the present disclosure. As illustrated in FIG. 11, the double helix filament 1000 may include a first filament 1111 and a second filament 1112. In some embodiments, the first filament 1111 and the second filament 1112 may be arranged side by side. For example, the first filament 1111 and the second filament 1112 may be arranged side by side along a radial direction of the double helix filament in which the first filament 1111 may be arranged on an inner side (or outer side) of the second filament 1112 along the radial direction of the double helix filament.

When the first filament 1111 and the second filament 1112 are powered by a power source (not shown in FIGS. 10A, 10B and 11), a first direction of a first current flow of the first filament 1111 may be opposite to a second direction of a second current flow of the second filament 1112, such that a first force (e.g., a first ampere force) on the first filament 1111 due to the magnetic field B is in line with and in an opposite direction to a second force (e.g., a second ampere force) on the second filament 1112 due to the magnetic field B. For example, as illustrated in FIG. 11, "x" refers to that the first direction of the first current flow of the first filament 1111 is perpendicular to the paper surface inward, and "•" refers to that the second direction of the second current flow of the second filament 1112 is perpendicular to the paper surface outward. The first force F1 on the first filament 1111 due to the magnetic field B may be in line with and in an opposite direction to the second direction of the second force F2 on the second filament 1112 due to the magnetic field B. For example, the first direction of the first force F1 on the first filament 1111 may be radially outward, and the second direction of the second force F2 on the second filament 1112 may be radially inward.

In some embodiments, the first filament 1111 and the second filament 1112 may be two separate filaments. For example, two separate filaments may be wound along the filament axis direction to form a first helix filament (i.e., the first filament) and a second helix filament (i.e., the second filament), respectively. Accordingly, the manufacture of the double helix filament may be simple and convenient. In this situation, two ends of the first filament, and two ends of the second filament may be power by the power source, respectively, such that the first direction of the first current flow of the first filament is opposite to the second direction of the second current flow of the second filament.

In some embodiments, the first filament 1111 and the second filament 1112 may be formed by a single filament. That is, the first filament and the second filament may be two portions of a single filament. For example, a first portion of a filament may be wound along the filament axis direction to form the first helix filament (i.e., the first filament). Then the filament may be bent, and a second portion of the filament may be wound along a direction opposite to the filament axis direction to form the second helix filament (i.e., the second filament). In this situation, two ends of the single filament may be power by the power source, and the first direction of the first current flow of the first filament may be opposite to the second direction of the second current flow of the second filament.

In some embodiments, a first current value of the first current flow of the first filament 1111 and a second current value of the second current flow of the second filament 1112 may be equal. For example, if the first filament 1111 and the second filament 1112 are two separate filaments, an end of the first filament 1111 may be electrically connected to an end of the second filament 1112 such that the first current value of the first current flow of the first filament 1111 and the second current value of the second current flow of the second filament 1112 are equal, and the first direction of the first current flow of the first filament is opposite to the second direction of the second current flow of the second filament. As another example, the first filament 1111 and the second filament 1112 may be powered by a power source, respectively, such that the first current value of the first current flow of the first filament 1111 and the second current value of the second current flow of the second filament 1112 are equal, and the first direction of the first current flow of the first filament is opposite to the second direction of the second current flow of the second filament. As a further example, if the first filament 1111 and the second filament 1112 are two portions of a single filament, the single filament may be powered by a power source such that the first current value of the first current flow of the first filament 1111 and the second current value of the second current flow of the second filament 1112 are equal, and the first direction of the first current flow of the first filament 1111 is opposite to the second direction of the second current flow of the second filament 1112. Accordingly, the strength of the first force on the first filament 1111 due to the magnetic field B may be equal to the strength of the second force on the second filament 1112 due to the magnetic field B. The first force and the second force may be (substantially) counterbalanced.

In some embodiments, the cathode heater may include a supporting component 1120 (also referred to as a second component illustrated in FIGS. 4-9B). The supporting component 1120 may enclose at least a portion of the first filament 1111 or the second filament 1112. For example, at least the portion of the first filament 1111 or the second filament 1112 may be embedded in the supporting component 1120. The supporting component 1120 may be made of a high temperature resistant and electrically insulating material. In some embodiments, a cross section of the supporting component 1120 may be circular, elliptical, rectangular, trapezoidal, or parallelogram. In some embodiments, the supporting component 1120 may be formed as one body for achieving a high mechanical strength. The high-strength support element may facilitate to prolong the cathode's service life and improve its use reliability. The supporting component 1120 may protect and support the first filament 1111 and the second filament 1112, and improve the structural stability of the cathode heater. For example, the first filament 1111 and the second filament 1112 may be embedded in the supporting component 1120, respectively, such that the first filament 1111 and the second filament 1112 are separated by supporting component 1120. The interference between the first filament 1111 and the second filament 1112 may be reduced or avoided, and the operation stability of the cathode heater may be improved. More descriptions of the supporting component 1120 may be found elsewhere in the present disclosure (e.g., FIGS. 4-9B, and descriptions thereof).

Conventionally, the cathode heater may be a single helix filament. When the single helix filament is powered on, a current in the single helix filament may be a one-way current, for example, the current flowing from an end of the single helix filament to the other end of the single helix filament. When the single helix filament is disposed in the magnetic field B. The direction of the magnetic field B may be parallel to a filament axis direction of the single helix filament. The direction of the force on the single helix filament due to the magnetic field B may be radially inward (or radially outward), which may cause the single helix filament to shrink (or expand). When the power in the single helix filament is turned off, the shrunk (or expanded) single helix filament may restore once the force disappears. Since the single helix filament is frequently shrunk (or expanded) and restores, such deformation of the single helix filament may cause damage to the single helix filament or a supporting component, and accordingly reduce the service life of the single helix filament, and the service life of the cathode.

According to some embodiments of the present disclosure, the cathode heater may include at least one filament in a double helix configuration. Compared with a filament in a cylindrical configuration, by using the filament in a helix configuration (e.g., a double helix configuration), the heating power of the cathode heater may be improved. In addition, the double helix filament may include the first filament 1111 and the second filament 1112. When the first filament 1111 and the second filament 1112 are powered by a power source, the first direction of the first current flow of the first filament 1111 may be opposite to the second direction of the second current flow of the second filament 1112, such that the first force on the first filament 1111 due to the magnetic field B is in line with and in an opposite direction to a second force on the second filament 1112 due to the magnetic field B. Accordingly, the first force on the first filament and the second force on the second filament may be (substantially) counterbalanced, which may reduce or avoid the deformation and/or prolong the service life of the cathode heater.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the double helix filament 1000 may also be disposed in one or more other magnetic fields. The strengths and the directions of the one or more other magnetic fields may be the same as, or different from, the strength and the direction of the magnetic field B. For example, the magnetic field B may be a component of a total magnetic field.

In some embodiments, a first length of the first filament 1111 may be the same as or different from a second length of the second filament 1112. In some embodiments, a first cross-sectional area of the first filament 1111 may be the same as or different from a second cross-sectional area of the second filament 1112. For example, if the first filament 1111 and the second filament 1112 are two separate filaments, the first cross-sectional area of the first filament 1111 is the same as the second cross-sectional area of the second filament 1112, and the first length of the first filament 1111 are greater than the second length of the second filament 1112, the voltage applied to the first filament 1111 may be different from the voltage applied to the second filament 1112 such that the first current value of the first current flow of the first filament 1111 and the second current value of the second current flow of the second filament 1112 are equal.

Figure 12A:
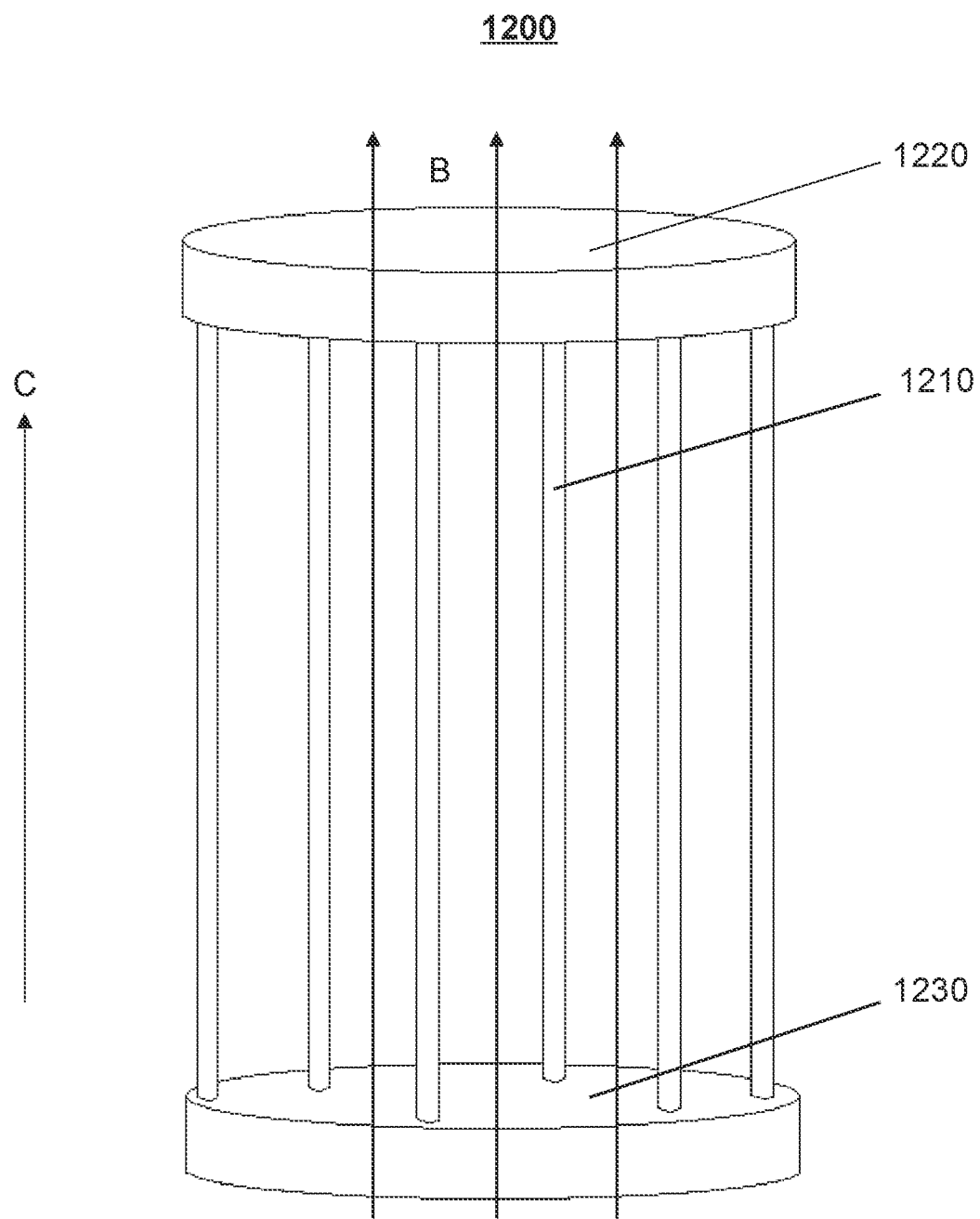
FIG. 12A is a schematic diagram illustrating an exemplary cathode heater according to some embodiments of the present disclosure.
Figure 12B:
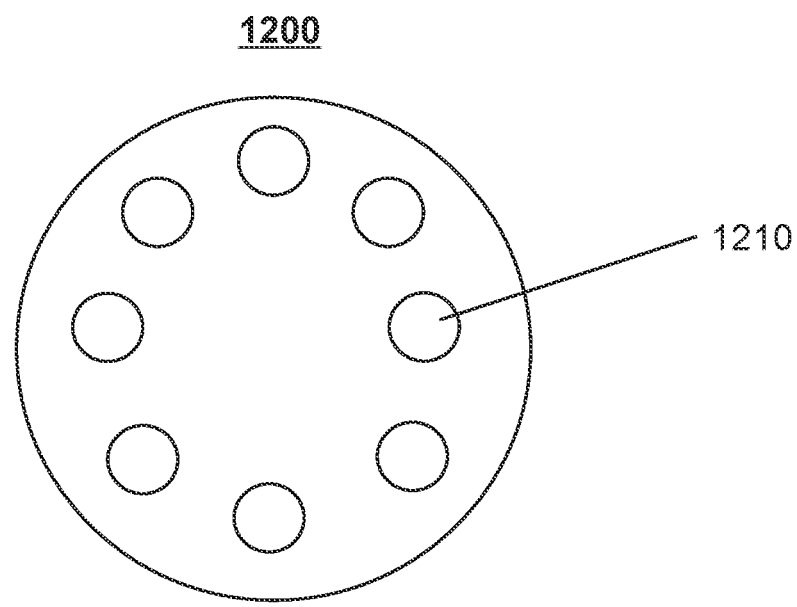
FIG. 12B is a top view of an exemplary cathode heater according to some embodiments of the present disclosure.

FIG. 12A is a schematic diagram illustrating an exemplary cathode heater according to some embodiments of the present disclosure. FIG. 12B is a top view of an exemplary cathode heater according to some embodiments of the present disclosure.

As illustrated in FIGS. 12A, and 12B, a cathode heater 1200 may include a plurality of filaments 1210. Each filament of the plurality of filaments 1210 may be of a columnar configuration (e.g., a cylindrical configuration). The plurality of filaments 1210 may be arranged in a cage configuration. For example, the plurality of filaments 1210 may be arranged along a circumferential direction of the cathode heater. An interval between adjacent filaments 1210 may be the same or different. In some embodiments, an extending direction C of the each filament of the plurality of filaments 1210 may be (substantially) parallel.

In some embodiments, the cathode heater 1200 may be disposed in a magnetic field B. In some embodiments, the magnetic field B may be generated by a microwave source as described in FIG. 3. A direction of the magnetic field B may be (substantially) parallel to the extending direction C of the each filament of the plurality of filaments 1210. When the plurality of filaments 1210 are powered by a power source, a direction of a current flow of the each filament 1210 may be the same or opposite. The direction of the current flow of the each filament 1210 may be (substantially) parallel to the direction of the magnetic field B such that the each filament 1210 is not subjected to a force (e.g., an electromagnetic force) due to the magnetic field B, which may reduce or avoid the deformation of the filament 1210 by the force. The service life of the cathode heater 1200 may be prolonged.

In some embodiments, a cross section of the each filament 1210 may be circular, elliptical, rectangular, trapezoidal, parallelogram, or the like. The cross section of the each filament 1210 may be the same or different. For example, the shape and the area of the cross section of the each filament 1210 may be the same. When a same voltage is applied to the each filament 1210, the current flow of the each filament 1210 may be the same.

In some embodiments, the cathode heater 1200 may include any number (or count) of filaments 1210. For example, the cathode heater 1200 may include two, six, eight, nine, etc., filaments 1210. The number (or count) of the filaments 1210 may be determined based on actual needs (e.g., desired heating power, a size limitation of the cathode heater, cost of the cathode heater). For example, if the desired heating power of the cathode heater 1200 is relatively high, the number (or count) of the filaments 1210 may need to be large. If the cost of the cathode heater 1200 needs to be reduced, the number (or count) of the filaments 1210 may be reduced.

In some embodiments, as illustrated in FIG. 12A, the cathode heater 1200 may include a first connection member 1220 and a second connection member 1230. The first connection member 1220 may be operably connected to a first end of the cathode heater 1200. The second connection member 1230 may be operably connected to a second end of the cathode heater 1200. The cathode heater 1200 may be powered by a power source via the first connection member 1220 and the second connection member 1230. For example, an end of each filament 1210 may be operably connected to the first connection member 1220, and the other end of the filament 1210 may be operably connected to the second connection member 1230. Each filament 1210 may be powered by the power source via the two ends operably connected to the first connection member 1220 and the second connection member 1230, respectively. As another example, the plurality of filament 1210 may include a first filament, a second filament, . . . , and a nth filament. An end of the first filament may be operably connected to the first connection member 1220, the other end of the first filament may be operably connected to an end of the second filament, the other end of the second filament may be operably connected to an end of a third filament, and so on, an end of the (n-1)th filament may be operably connected to an end of the nth filament, the other end of the nth filament may be operably connected to the second connection member 1230. That is, the plurality of filament 1210 may be connected in series. In addition, the first connection member 1220 and the second connection member 1230 may provide mechanical support for the plurality of filaments 1210, thereby improving the structural stability of the cathode heater 1200.

In some embodiments, the cathode heater 1200 may include a supporting component (not shown in FIGS. 12A-12B) (also referred to as a second component illustrated in FIGS. 4-9B). The supporting component may enclose at least a portion of the plurality of filaments 1210. For example, the at least a portion of the plurality of filaments 1210 may be embedded in the supporting component. The supporting component may be made of a high temperature resistant and electrically insulating material. More descriptions of the supporting component may be found elsewhere in the present disclosure (e.g., FIGS. 4-9B, and descriptions thereof).

The supporting component may be configured based on actual needs (e.g., structural stability requirements of the cathode heater 1200). For example, if the cross-sectional area of the filament 1210 is relatively large, and/or the structural stability of the cathode heater 1200 is relatively good, the supporting component may not be provided. If the cross-sectional area of the filament 1210 is relatively small, and the structural stability of the cathode heater 1200 is relatively poor, the supporting component may be provided to improve the structural stability of the cathode heater 1200.

According to some embodiments of the present disclosure, the cathode heater 1200 may include a plurality of filaments 1210. Each filament of the plurality of filaments 1210 may be of a cylindrical configuration. When the plurality of filaments 1210 are powered by a power source, the direction of the current flow in each filament of the plurality of filaments 1210 may be (substantially) parallel to the direction of the magnetic field B such that the each filament 1210 is not subjected to a force, which may reduce or avoid the deformation of the filament. The service life of the cathode heater 1200 may be prolonged. In addition, by adjusting the number (or count) of the plurality of filaments 1210, the heating power of the cathode heater 1200 may be adjusted. Furthermore, the plurality of filaments 1210 may be arranged in a cage configuration, which may improve the structural stability of the cathode heater 1200.

Figure 13A:
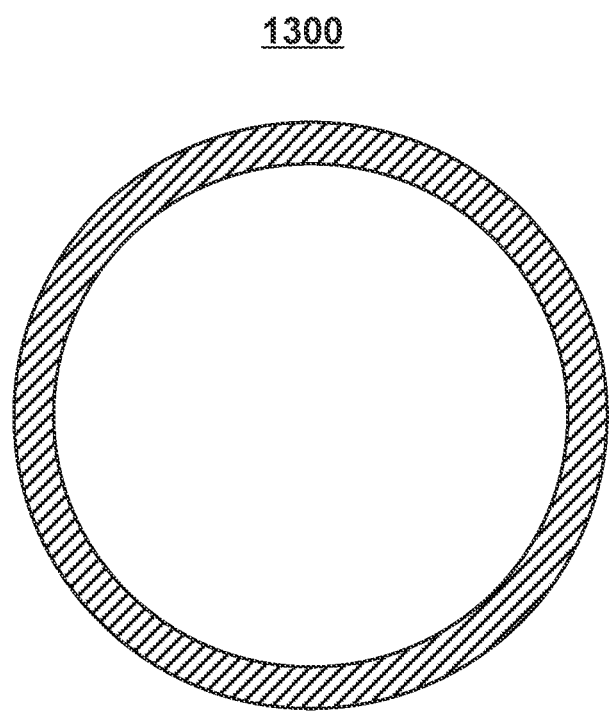
FIG. 13A is a top view of an exemplary cathode heater according to some embodiments of the present disclosure.
Figure 13B:
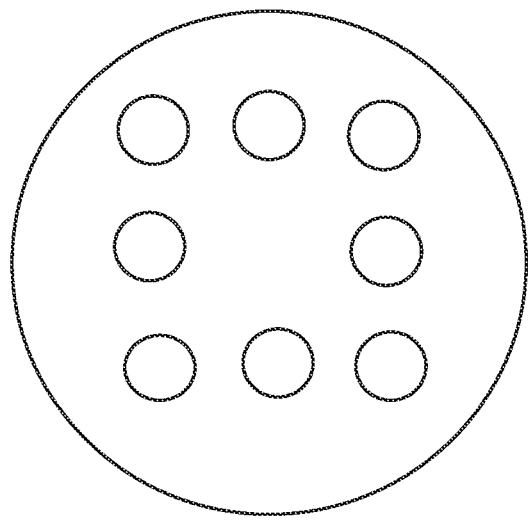
FIG. 13B is a top view of an exemplary cathode heater according to some embodiments of the present disclosure.
Figure 13C:
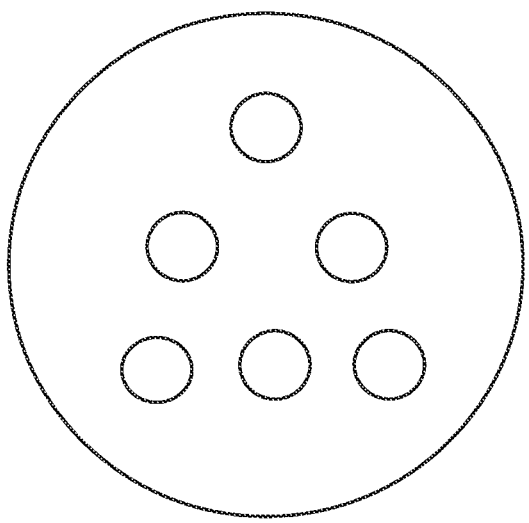
FIG. 13C is a top view of an exemplary cathode heater according to some embodiments of the present disclosure.

FIG. 13A is a top view of an exemplary cathode heater according to some embodiments of the present disclosure. As illustrated in FIG. 13A, a cathode heater 1300 may include a ring-shaped filament. The structural stability and the heating power of the ring-shaped filament may be relatively high.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the plurality of filaments 1210 may be arranged in an array of various shapes, such as an array of the shape of a ring, a circle, a square (e.g., an array 1310 illustrated in FIG. 13B), or a triangle (e.g., an array 1320 illustrated in FIG. 13C).

FIG. 14 is a schematic diagram illustrating an exemplary thermionic emitter according to some embodiments of the present disclosure.

As illustrated in FIG. 14, a thermionic emitter 1400 may include a substrate component 1410 and an electron emission layer 1420. A cathode heater (e.g., the cathode heater 411 illustrated in FIG. 4, the cathode heater 511 illustrated in FIG. 5, the cathode heater 711 illustrated in FIGS. 6-7, the cathode heater 811 illustrated in FIGS. 8A-9B, the double helix filament 1000 illustrated in FIG. 10, the cathode heater 1200 illustrated in FIGS. 12A and 12B) may be disposed inside the substrate component 1410. The substrate component 1410 may be configured to support the electron emission layer 1420. In some embodiments, the substrate component 1410 may be of a cylindrical configuration. The substrate component 1410 may be made of molybdenum, tungsten, molybdenum, rhenium, iridium, or the like, or any combination thereof. The electron emission layer 1420 may be configured to release electrons when the electron emission layer 1420 is heated by the cathode heater. The electron emission layer 1420 may be disposed on an outer wall of the substrate component 1410. For example, thermionic emission materials may be coated on the outer wall of the substrate component 1410 to form the electron emission layer 1420.

In some embodiments, the electron emission layer 1420 may include at least one discontinuity. As used herein, a discontinuity refers to an interruption in physical characteristics or structure of an object (e.g., the electron emission layer 1420). For example, the electron emission layer 1420 may include the at least one discontinuity such that the electron emission layer 1420 is divided into portions.

In some embodiments, the electron emission layer 1420 may include at least one groove 1430 configured to cause the at least one discontinuity in the electron emission layer 1420. In some embodiments, the at least one groove 1430 may extend along an axial direction (e.g., an axial direction D illustrated in FIG. 14), a circumferential direction, and/or other direction of the substrate component 1410. For example, as illustrated in FIG. 14, a plurality of grooves 1430 may extend along the axial direction D of the substrate component 1410. In some embodiments, at least a portion of the plurality of grooves 1430 may extend in a parallel direction and be equispaced. As used herein, "a plurality of grooves being equispaced" refers to that the plurality of grooves are spaced apart by equal distances.

Figure 15:
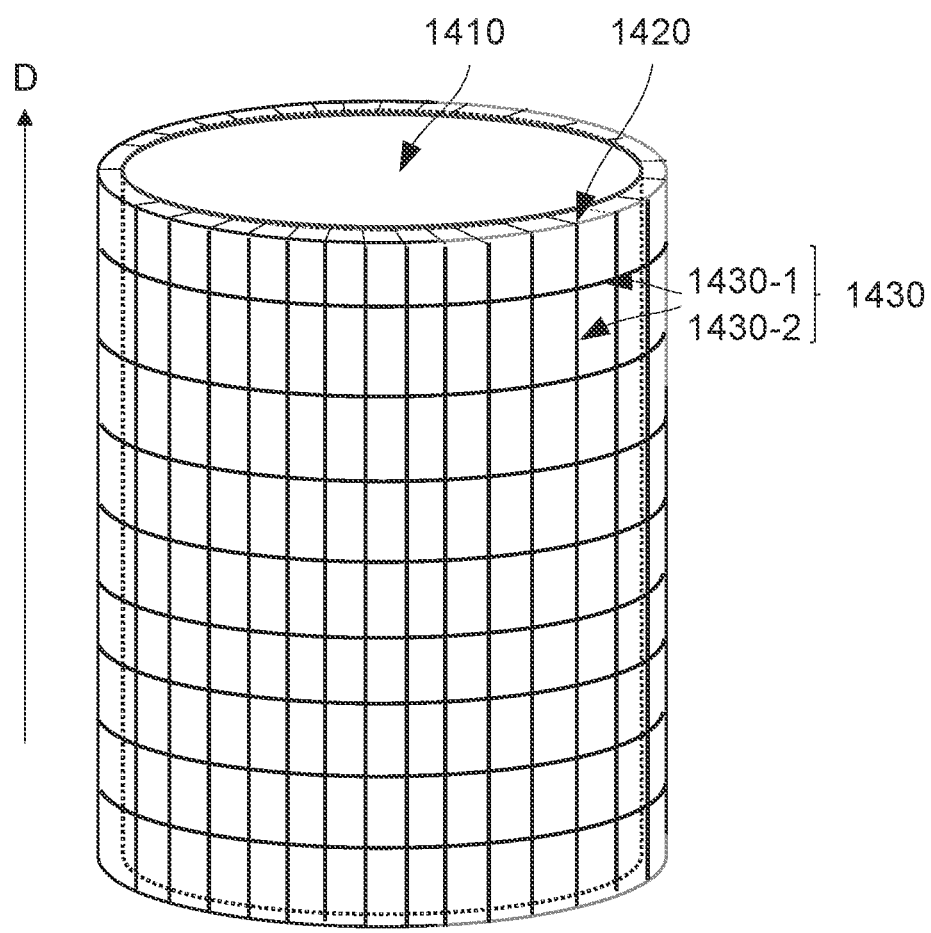
FIG. 15 is a schematic diagram illustrating an exemplary thermionic emitter according to some embodiments of the present disclosure.
Figure 16:
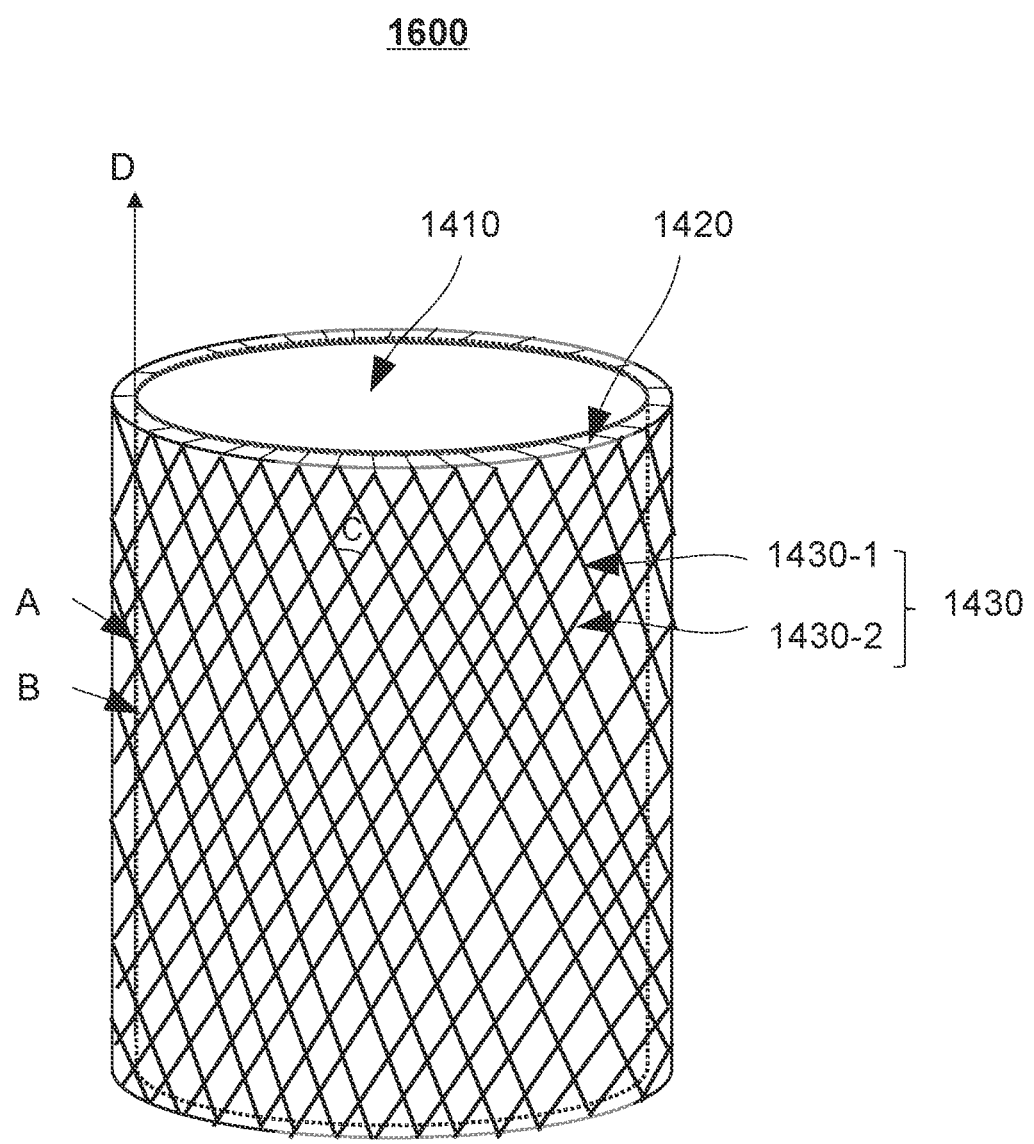
FIG. 16 is a schematic diagram illustrating an exemplary thermionic emitter according to some embodiments of the present disclosure.

In some embodiments, the thermionic emitter 1400 may include at least one first groove (e.g., a first groove 1430-1 illustrated in FIGS. 15-16) and at least one second groove (e.g., a second groove 1430-2 illustrated in FIGS. 15-16). A first extending direction of the at least one first groove may be different from a second extending direction of the at least one second groove. More descriptions of the first groove and the second groove may be found elsewhere in the present disclosure (e.g., FIGS. 15-16, and the descriptions thereof).

Figure 17A:
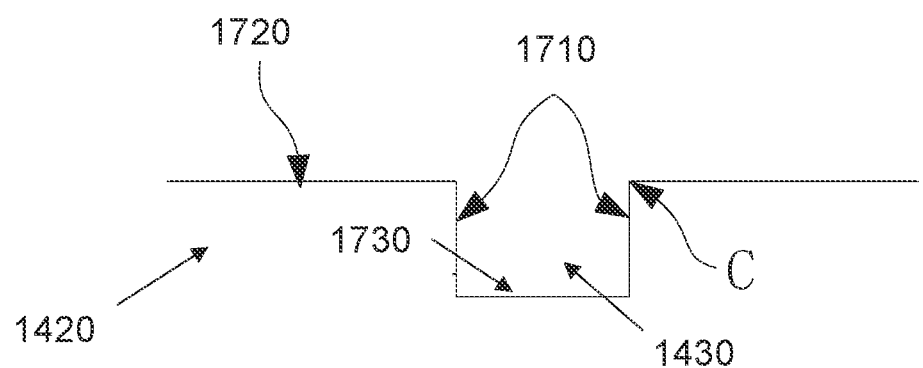
FIGS. 17A-17C are schematic diagrams illustrating cross-sectional views of exemplary grooves according to some embodiments of the present disclosure.
Figure 17B:
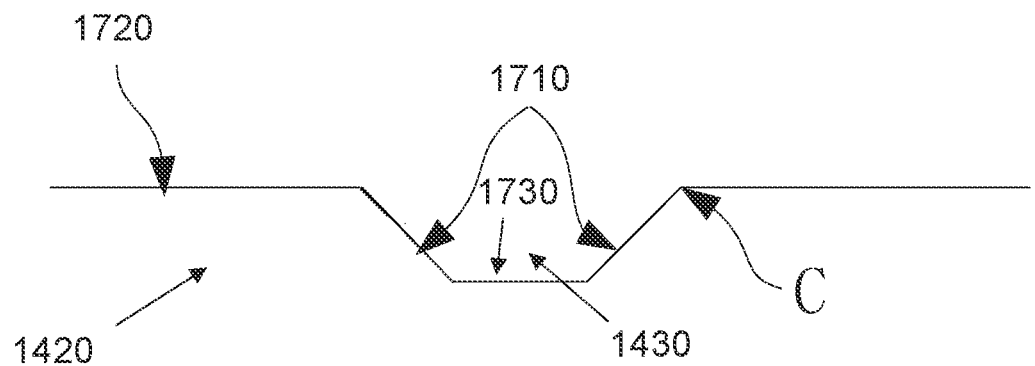
Figure 17C:
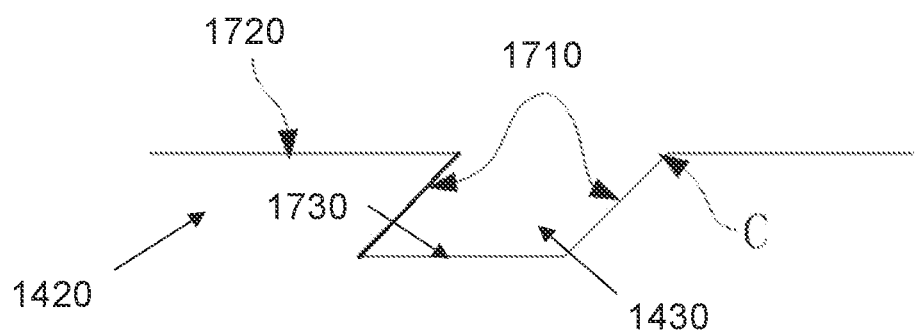

In some embodiments, a longitudinal section of the at least one groove 1430 may be rectangular, trapezoidal, parallelogram, or the like. As used herein, a longitudinal section of a groove refers to a section along an extending direction of the groove. In some embodiments, a cross section of the at least one groove 1430 may be rectangular, trapezoidal, parallelogram, or the like, as illustrated in FIGS. 17A-17C. As used herein, a cross section of a groove refers to a section along a direction perpendicular to the extending direction of the groove.

In some embodiments, a depth and/or a length of at least two of the at least one groove 1430 may be the same or different. As used herein, "a depth of a groove" refers to its length along a radial direction of the substrate component 1410, e.g., the depth d illustrated in FIG. 14. For example, the depth of the groove 1430 may be a distance between an outer surface (e.g., a surface 1720 illustrated in FIGS. 17A-17C) of the electron emission layer 1420 and an outer surface of the groove 1430 (e.g., a surface 1730 illustrated in FIGS. 17A-17C) along a radial direction of the substrate component 1410. As used herein, "a length of a groove" refers to its shortest length between a start point and an end point of the groove along an extending direction of the groove, e.g., the length L illustrated in FIG. 14. As used herein, an "outer surface" of the electron emission layer 1420 refers to a surface of the electron emission layer 1420 that is exposed to air or away from the substrate component 1410, compared with the inner surface of the electron emission layer 1420. As used herein, an "inner surface" of the electron emission layer 1420 refers to a surface of the electron emission layer 1420 that is not exposed to air or in contact with the substrate component 1410.

In some embodiments, the depth of the at least one groove 1430 may be less than or equal to a thickness of the electron emission layer 1420. As used herein, "a thickness of an electron emission layer" refer to the distance between an outer surface of the electron emission layer and an inner surface of the electron emission layer. In some embodiments, when the at least one groove 1430 extends along the axial direction of the substrate component 1410, and the at least one groove 1430 has a straight-line shape, the length of the at least one groove 1430 may be less than or equal to a length of the electron emission layer 1420. For example, as illustrated in FIG. 14, the length of each groove of the plurality of grooves 1430 may be equal to the length of the electron emission layer 1420 along the axial direction, and the depth of the each groove of the plurality of grooves 1430 may be equal to the thickness of the electron emission layer 1420 such that the plurality of grooves 1430 may penetrate through the electron emission layer 1420.

In some embodiments, the electron emission layer 1420 may include any number (or count) of grooves 1430. For example, the electron emission layer 1420 may include two grooves 1430 that are parallel to each other and extending through the entire length of the electron emission layer 1420. The two grooves 1430 may evenly divide the electron emission layer 1420 into two portions. Accordingly, when the thermionic emitter 1400 is heated by the cathode heater, each portion of the electron emission layer 1420 may be deformed (e.g., expanded) (substantially) uniformly, thereby avoiding uneven deformation of the electron emission layer 1420. The number (or count) of the grooves 1430 and the positions of the grooves 1430 may be determined based on actual needs (e.g., a desired performance of the thermionic emitter 1400). That is, the number (or count) of divided portions and/or shapes of the divided portions of the electron emission layer 1420 may be determined based on actual needs. For example, if the electron emission layer 1420 is expected to undergo relatively large thermal expansion and contraction, the number (or count) of the grooves 1430 may need to be increased.

During the use of the thermionic emitter 1400, when the electron emission layer 1420 is heated by the cathode heater, and the temperature of the electron emission layer 1420 increases, the electron emission layer 1420 may have a tendency to expand. When the cathode heater is powered off, and the temperature of the electron emission layer 1420 decreases, the expanded electron emission layer 1420 may have a tendency to shrink. The electron emission layer 1420 may be squeezed or stretched due to thermal expansion and contraction, and a crack may be generated. According to some embodiments of the present disclosure, the electron emission layer 1420 disposed on the outer wall of the substrate component 1410 may include at least one discontinuity (e.g., at least one groove). The at least one discontinuity may provide a space for accommodating a deformation of the electron emission layer 1420 due to thermal expansion and contraction. The ability of the electron emission layer 1420 to accommodate the deformation due to thermal expansion and contraction may be improved. The surface stress caused by the thermal expansion or an uneven surface temperature distribution of the electron emission layer 1420 may be dispersed by the at least one discontinuity. The risk of cracking of the electron emission layer 1420 may be reduced, and the electron emission efficiency of the thermionic emitter 1400 may be improved. The service life of the thermionic emitter 1400 may be prolonged.

In some embodiments, the thermionic emitter 1400 may include a filling layer (not shown in FIG. 14) disposed in the at least one groove 1430. In some embodiments, the filling layer may be configured to adjust the performance of the thermionic emitter 1400. For example, the filling layer may reduce the volatilization rate of the material of the electron emission layer 1420. As another example, the filling layer may adjust a temperature distribution of the electron emission layer 1420. In some embodiments, the material of the filling layer may be selected according to actual needs of the thermionic emitter 1400 to improve the performance of the thermionic emitter 1400. For example, the filling layer may be made of a material that promotes electron emission, such as iridium. As another example, the filling layer may be made of a material that inhibits electron emission, such as hafnium. As still another example, the filling layer may be made of a volatile material. As still another example, the filling layer may be made of a ceramic material (e.g., aluminum oxide) with desirable heat transfer and heat dissipation properties.

FIG. 15 is a schematic diagram illustrating an exemplary thermionic emitter according to some embodiments of the present disclosure. A thermionic emitter 1500 may be similar to the thermionic emitter 1400, except for certain features as described below.

As illustrated in FIG. 15, the thermionic emitter 1500 may include the substrate component 1410 and the electron emission layer 1420. The electron emission layer 1420 may include a plurality of first groove 1430-1 and a plurality of second groove 1430-2. The plurality of first grooves 1430-1 may extend along the circumferential direction of the substrate component 1410, and the plurality of second grooves 1430-2 may extend along the axial direction (e.g., an axial direction D illustrated in FIG. 15) of the substrate component 1410. The plurality of first grooves 1430-1 may extend in a parallel direction and be equispaced. The plurality of second grooves 1430-2 may extend in a parallel direction and be equispaced. The electron emission layer 1420 may be divided into a plurality of square grids or rectangular grids.

FIG. 16 is a schematic diagram illustrating an exemplary thermionic emitter according to some embodiments of the present disclosure. A thermionic emitter 1600 may be similar to the thermionic emitter 1500, except for certain features.

As illustrated in FIG. 16, the thermionic emitter 1600 may include the substrate component 1410 and the electron emission layer 1420. The electron emission layer 1420 may include a plurality of first groove 1430-1 and a plurality of second groove 1430-2. The plurality of first grooves 1430-1 may extend along a first direction of the substrate component 1410, and the plurality of second grooves 1430-2 may extend along a second direction of the substrate component 1410. The first direction and the axial direction of the substrate component 1410 may form a first angle A. The second direction and the axial direction of the substrate component 1410 may form a second angle B. The first angle A may be different from the second angle B. The first angle A and the second angle B may be greater than 0° and less than 180°. In some embodiments, an angle C between the first direction and the second direction may be an acute angle (e.g., 30°, 60°), an obtuse angle (e.g., 120°, 150°), or a right angle (e.g., 90° as illustrated in FIG. 15).

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the at least one groove 1430 may have any shape. For example, the at least one groove 1430 may have a straight-line shape, a curved line shape, a polyline shape (e.g., an "L" shape, a "Z" shape), or the like. In some embodiments, the at least one groove 1430 may be arranged continuously or intermittently along its extending direction.

FIGS. 17A-17C are schematic diagrams illustrating cross-sectional views of exemplary grooves according to some embodiments of the present disclosure.

As illustrated in FIGS. 17A-17C, a cross section of the groove 1430 may be rectangular, trapezoidal, or parallelogram. The groove 1430 may include a side surface 1710. The side surface 1710 and an outer surface 1720 of the electron emission layer 1420 may be arranged at an angle C, such that the side surface 1710 of the groove 1430 and the outer surface 1720 of the electron emission layer 1420 form an angular boundary (rather than a rounded boundary). The angle C may be greater than 0° and less than 180°. For example, the angle C may be greater than 0°, and less than or equal to 90°. Accordingly, a plurality of sharp edges may be formed between the side surface 1710 of the groove 1430 and the outer surface 1720 of the electron emission layer 1420. Since an electric field strength of the sharp edge is relatively strong, and electrons are easily emitted from the plurality of sharp edges than from the remaining portions of the electron emission layer 1420, the emission efficiency of a thermionic emitter (e.g., the thermionic emitter 1400, the thermionic emitter 1500, the thermionic emitter 1600) may be improved compared to without the sharp edges (or grooves 1430). The temperature required for the electron emission layer 1420 to emit electrons may be reduced, and the service life of the thermionic emitter may be prolonged.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 18:
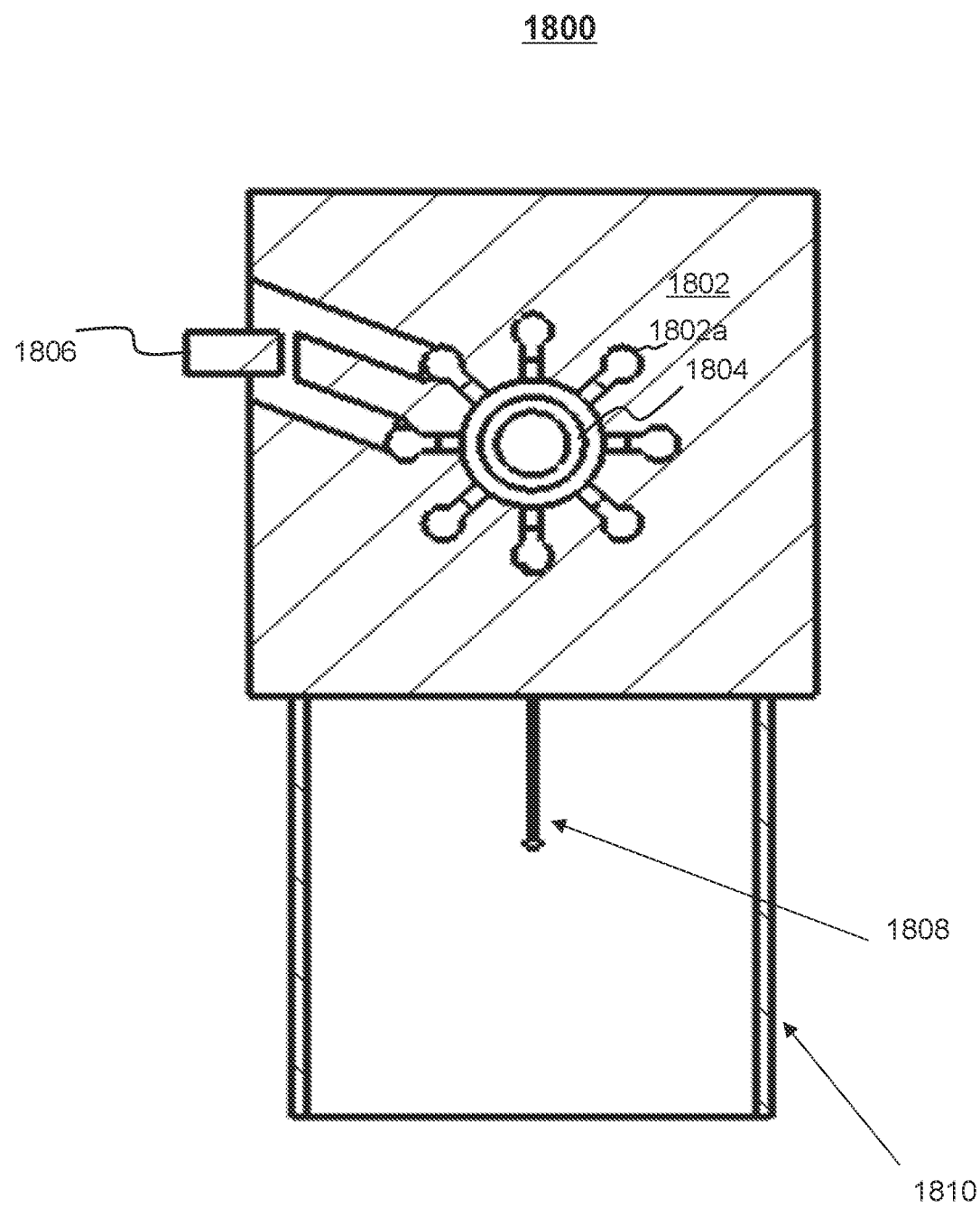
FIG. 18 illustrates a cross-sectional view of an exemplary microwave source according to some embodiments of the present disclosure.

FIG. 18 illustrates a cross-sectional view of an exemplary microwave source according to some embodiments of the present disclosure. Merely for illustration, microwave source 1800 illustrated in FIG. 18 may be a magnetron. The magnetron may be a tunable magnetron. The microwave source 1800 may include an anode block 1802, a cathode 1804 centered in the anode block 1802, a tuning element 1806, a microwave transmitter 1808, and a transmission waveguide 1810. As described in connection with FIGS. 3A and 3B, the anode block 1802 may include a plurality of resonant cavities 1802a. The resonant cavities 1802a may exist in the form of the hole-and-slot type illustrated in FIG. 3B. The cathode 1804 may be removably positioned in the center of the anode block. As described in connection with FIGS. 4-17C, the cathode 1804 may include a cathode heater, and a thermionic emitter. More descriptions regarding the cathode may be found elsewhere in the present disclosure (e.g., FIGS. 4-17C, and the descriptions thereof).

The tuning element 1806 may be configured to adjust a resonant frequency of the microwave source 1800. The resonant frequency may be changed by varying the inductance or capacitance of the resonant cavities of the microwave source. In some embodiments, the tuning element 1806 may be inserted into the hole portion of the hole-and-slot cavities. The tuning element 1806 may change the capacitance of the resonant cavities by altering the ratio of surface areas to cavity volume in a high-current region. The resonant frequency of the microwave source 1800 may be adjusted higher or lower through an insertion or removement of the tuning element 1806. For example, when the tuning element 1806 is inserted into the anode hole, the capacitance of the cavity can be increased, thereby the resonant frequency may be decreased. In some embodiments, the microwave source 1800 may include multiple tuning elements 1806 operably connected to each resonant cavity 1802a. Merely for illustrative purposes, just one tuning element 1806 is illustrated. In some embodiments, the tuning element 1806 may be made of an electrically conductive material (e.g., copper, aluminum, or other metal materials).

The microwave transmitter 1808 may be configured to transmit the microwaves generated by the microwave source 1800. The microwaves may be transmitted into the transmission waveguide 1810 (e.g., the transmission waveguide illustrated in FIG. 2). Then transmission waveguide 1810 may transmit the microwaves to an accelerator tube (e.g., the accelerator tube 210) in order to provide the kinetic energy to accelerate electrons in the accelerator tube.

Figure 19:
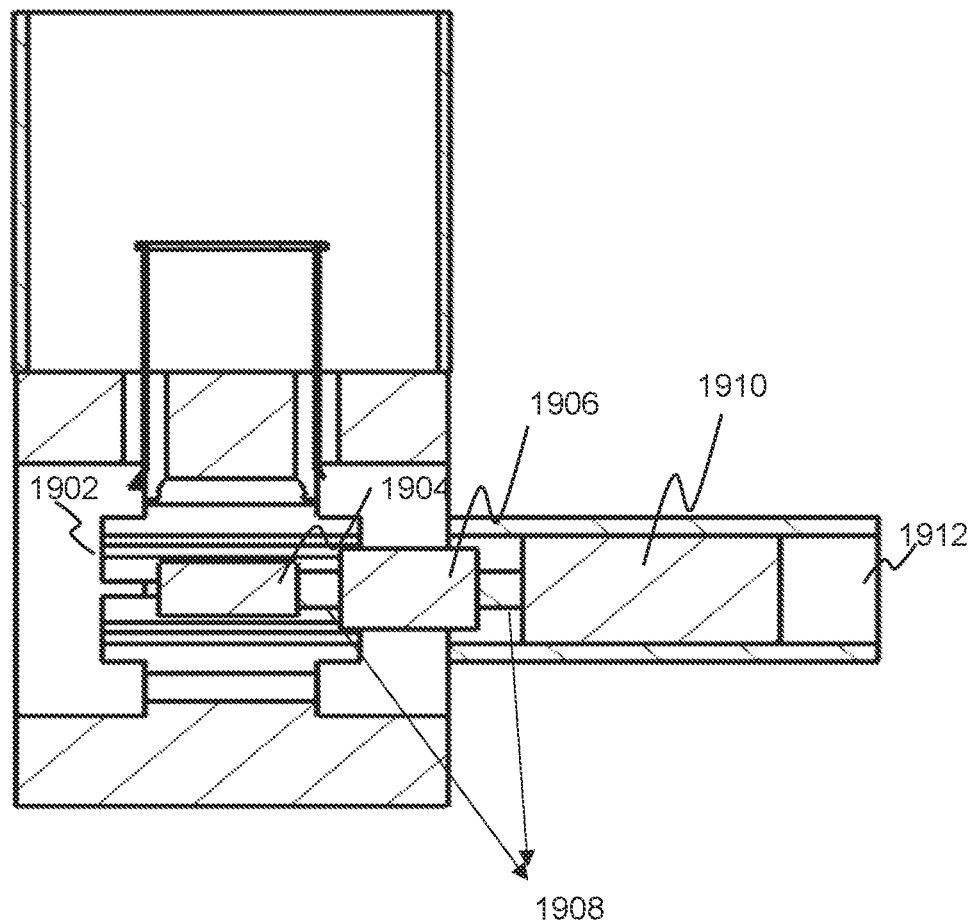
FIG. 19 illustrates a cross-sectional view of an exemplary microwave source according to some embodiments of the present disclosure.

FIG. 19 illustrates a cross-sectional view of an exemplary microwave source according to some embodiments of the present disclosure. As illustrated in FIG. 19, microwave source 1900 may be a multi-cathode microwave source (e.g., a multi-cathode magnetron). The microwave source 1900 may include an anode block 1902 and multiple cathodes, such as a first cathode 1904 and a second cathode 1906. In some embodiments, the multiple cathodes may be removably positioned in the center of the anode block 1902. In some embodiments, when an individual cathode (e.g., the first cathode 1904 or the second cathode 1906) of the multiple cathodes is removably positioned in the center of the anode block, microwaves having a specific frequency (e.g., a specific microwave power) are generated in response to an occurrence of a resonance effect caused by the anode block and the cathode. More descriptions regarding the anode block and the cathode may be found elsewhere in the present disclosure (e.g., FIGS. 3A-17C, and the descriptions thereof).

In some embodiments, respective diameters of the multiple cathodes may be different. In some embodiments, the diameters of at least two of the multiple cathodes may be different. For example, the first cathode diameter may be 18 mm and the second cathode diameter may be 22 mm. In some embodiments, the microwave source 1900 may include a connector 1908. The multiple cathodes may be mechanically connected to each other by the connector 1908. The connector 1908 (e.g., a support rod) may be configured to support and connect each cathode. The connector 1908 may be made of an insulative material. In some embodiments, the microwave source 1900 may include a limiting member 1910. An end of the connector 1908 may be operably connected to the limiting member 1910. In some embodiments, the microwave source 1900 may include a guide slot 1912. The limiting member 1910 may be disposed in the guide slot 1912. In some embodiments, the limiting member 1910 may move (e.g., slide) along the guide slot 1912 in order to position the cathode of the multiple cathodes. For example, when the limiting member 1910 is moved to a first location, the first cathode 1904 can be positioned in the center of the anode block 1902. When the limiting member 1910 is moved to a second location, the second cathode 1906 can be positioned in the center of the anode block 1902 and the first cathode 1904 may be moved out. In some embodiments, the limiting member 1910 may be driven by various driving devices. Exemplary driving devices may include a hydraulic driver, a pneumatic driver, an electric actuator. In some embodiments, the various driving devices may not cause interferences for the generation of microwaves.

An electronic efficiency of the microwave source (e.g., the magnetron) may rely on a ratio of diameters of the cathode and the anode block (also referred to as "diameter ratio"). When the dimeter ratio is in a specific range, the electron efficiency may be at an optimal value, and an output power of the microwave source may be maximum. For example, for an eight-cavities anode block, when the diameter ratio is in the rage of 0.37-0.42, the electronic efficiency of the magnetron may be optimal. As another example, for a twelve-cavities anode block, when the diameter ratio is in the range of 0.50-0.58, the electronic efficiency of the magnetron may be optimal. As a further example, for a sixteen-cavities anode block, when the diameter ratio is in the range of 0.60-0.66, the electronic efficiency of the magnetron may be optimal.

In some embodiments, the output power of the microwave source can be changed by varying the diameter ratio of the anode block to the cathode. In some embodiments, for a specific anode block, the diameter ratio can be changed by alternating the cathodes having different diameters. Merely for illustration, for a magnetron including a twelve-cavities anode block, its resonant frequency is 2998 MHz and maximum output power is 3.4 MW. Given that the diameter of the anode block is 34 mm. The maximum output power of the magnetron can be reached only if the diameter of the cathode in the range of 17-19.72 mm. It is understood that, when the diameter of a cathode is less than 17 mm or greater than 19.72 mm, the magnetron may output a relatively small microwave power. By arranging the constant anode block and one of the cathodes having different diameters, the magnetron may output alternative microwave powers. The alternative microwave powers may be used to generate radiation beams of different energies. For example, the diameter of the anode block 1902 is set as 34 mm and the diameter of the first cathode 1904 is set as 18 mm. When the anode block 1902 and the first cathode 1904 are powered on, the microwave source 1900 may output the maximum microwave power for accelerating electrons in the accelerator tube 210 to generate therapeutic radiation beams. The therapeutic radiation beams may be applied to the subject for eliminating tumor tissues. As another example, the diameter of the second cathode 1906 is set as 22 mm. When the anode block 1902 and the second cathode 1906 are powered on, the microwave source 1900 may output a relatively small microwave power for accelerating electrons in the accelerator tube 210 to generate imaging radiation beams. For the IGRT device, the imaging radiation beams may be used to image a region of interest (ROI) related to the subject. The radiotherapy procedure may be guided according to the ROI related information (e.g., a tumor region).

In some embodiments, the resonant frequency of the microwave source can be changed by alternating different cathodes. The resonant frequency of the microwave source may rely on an equivalent capacitance and inductance of the microwave source. For example, the resonant frequency, $f=1/\sqrt{LC}$, where L denotes the inductance and C denotes the equivalent capacitance. For the constant anode block, the larger the diameter of the cathode, the smaller the distance between the cathode and the anode block, thereby the equivalent capacitance becomes larger. The resonant frequency may be changed with the equivalent capacitance. In some embodiments, by switching cathodes of different diameters, different resonant frequency may be produced accordingly. In addition, the tuning element (e.g., the tuning element 1806) of the microwave source may slightly adjust the resonant frequency, such as ±5 MHz. The adjustable range of the resonant frequency of the microwave source may be enlarged due to the use of the multiple cathodes and the tuning element. It is understood that the frequencies of output microwaves may be changed by varying the characteristics (e.g., resonant frequencies) of the microwave source. Specific microwave frequencies may be produced when different cathodes are applied.

Various embodiments are provided herein with reference to a microwave source composed of an anode block and one or more cathodes. In some embodiments, the microwave source (e.g., a single-cathode microwave source) may include an anode block and a cathode centered in the anode block. In some embodiments, the microwave source (e.g., a multi-cathode microwave source) may include an anode block and multiple cathodes. The multiple cathodes may share the same anode block. In some embodiments, one of the multiple cathodes can be removably positioned in the anode block. Diameters of the multiple cathodes may be different. In response to an occurrence of a resonance effect caused by the anode block and the cathode positioned in the anode block, microwaves having a specific frequency may be generated. For example, when a first cathode is positioned in the anode block, first microwaves having a first frequency may be generated due to the resonant effect caused by the anode block and the first cathode. As another example, when a second cathode is positioned in the anode block, second microwaves having a second frequency may be generated due to the resonant effect caused by the anode block and the second cathode. The first frequency and the second frequency may be different. Different microwave powers can be output. Compared with a single-cathode microwave source, a multi-cathode microwave source may output alternative microwave powers and/or frequencies by grouping the anode block and a cathode of the multiple cathodes.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A microwave source, comprising:
   a cathode heater, wherein the cathode heater includes:
      a first component including at least one filament, and
      a second component enclosing at least a portion of the first component; and
   a thermionic emitter configured to release electrons when the thermionic emitter is heated by the cathode heater, wherein at least a portion of the second component of the cathode heater is in contact with the thermionic emitter and the thermionic emitter is configured to surround the cathode heater.

2. The microwave source of claim 1, wherein the at least a portion of the first component of the cathode heater is in contact with the second component of the cathode heater.

3. The microwave source of claim 2, wherein the at least a portion of the first component of the cathode heater is embedded in the second component of the cathode heater.

4. The microwave source of claim 1, wherein the cathode heater includes a third component, the first component and the second component being disposed between the third component and the thermionic emitter.

5. The microwave source of claim 4, wherein the cathode heater includes at least one fourth component configured to increase a structural stability of the third component.

6. The microwave source of claim 1, further comprising:
   a first connection member operably connected to a first end of the first component; and
   a second connection member operably connected to a second end of the first component, wherein the first component is powered by a power source via the first connection member and the second connection member.

7. The microwave source of claim 1, wherein the thermionic emitter includes:
   a substrate component, wherein the cathode heater is disposed inside the substrate component; and
   an electron emission layer disposed on an outer wall of the substrate component that includes at least one discontinuity.

8. The microwave source of claim 7, wherein the at least a portion of the second component of the cathode heater is in contact with the substrate component.

9. The microwave source of claim 7, wherein the electron emission layer includes at least one groove configured to cause the at least one discontinuity in the electron emission layer.

10. The microwave source of claim 9, wherein the at least one groove extends along an axial direction or a circumferential direction of the substrate component.

11. The microwave source of claim 9, wherein the electron emission layer includes a plurality of grooves, the plurality of grooves extending in a parallel direction and being equispaced.

12. A microwave source, comprising:
   a cathode heater including a double helix filament, wherein the double helix filament includes a first filament and a second filament; and
   a thermionic emitter configured to release electrons when the thermionic emitter is heated by the cathode heater and configured to surround the cathode heater;
   wherein when the first filament and the second filament are disposed in a magnetic field and powered by a power source, a first direction of a first current flow in the first filament is opposite to a second direction of a second current flow in the second filament such that a first force on the first filament due to the magnetic field is in line with and in an opposite direction to a second force on the second filament due to the magnetic field.

13. The microwave source of claim 12, wherein a first current value of the first current flow of the first filament and a second current value of the second current flow of the second filament are equal.

14. The microwave source of claim 13, wherein a direction of the magnetic field is parallel to a filament axis direction of the double helix filament.

15. The microwave source of claim 14, wherein a first diameter of the first filament is less than a second diameter of the second filament along a direction perpendicular to the filament axis direction of the double helix filament.

16. The microwave source of claim 12, wherein the cathode heater further comprises:
   a supporting component in which at least a portion of the first filament or the second filament are embedded.

17. A microwave source, comprising:
   a cathode heater including one or more filaments, wherein each filament of the one or more filaments is of a cylindrical configuration; and
   a thermionic emitter configured to release electrons when the thermionic emitter is heated by the cathode heater and configured to surround the cathode heater;
   wherein when the cathode heater is disposed in a magnetic field, a direction of the magnetic field is parallel to an extending direction of the each filament of the one or more filaments.

18. The microwave source of claim 17, wherein the cathode heater includes a plurality of filaments arranged in a cage configuration.

19. The microwave source of claim 17, further comprising:
   a first connection member operably connected to a first end of the cathode heater; and
   a second connection member operably connected to a second end of the cathode heater, wherein the cathode heater is powered by a power source via the first connection member and the second connection member.

20. The microwave source of claim 17, wherein the cathode heater further comprises:
   a supporting component in which at least a portion of the first filament or the second filament are embedded.

* * * * *